US005616797A

United States Patent [19]

Wilson et al.

[11] Patent Number: 5,616,797

[45] Date of Patent: Apr. 1, 1997

[54] N-(CARBONYL, CARBONIMIDOYL, CARBONOTHIOYL)SULFONAMIDE CHARGE CONTROL AGENTS AND TONERS AND DEVELOPERS

[75] Inventors: John C. Wilson; Peter S. Alexandrovich, both of Rochester; Steven M. Bonser, Fairport, all of N.Y.

[73] Assignee: Eastman Kodak Company, Rochester, N.Y.

[21] Appl. No.: 353,466

[22] Filed: Dec. 9, 1994

Related U.S. Application Data

[62] Division of Ser. No. 171,783, Dec. 22, 1993, Pat. No. 5,405,727.

[51] Int. Cl.$^6$ .......... C07C 307/02

[52] U.S. Cl. .......... 564/92; 560/9; 560/12; 562/426; 562/430; 562/432; 564/86; 564/87; 564/89; 564/88; 564/90; 564/93; 564/94

[58] Field of Search .......... 564/86, 87, 89, 564/94, 93, 92, 90, 88; 560/9, 12; 562/430, 426, 432

[56] References Cited

U.S. PATENT DOCUMENTS

| | | | |
|---|---|---|---|
| Re. 31,072 | 11/1982 | Jadwin et al. | 430/99 |
| 3,547,822 | 12/1970 | Miller | 430/99 |
| 3,577,345 | 5/1971 | Jacknow et al. | 430/110 |
| 3,632,512 | 1/1972 | Miller | 430/137 |
| 3,795,618 | 3/1974 | Kasper | 430/108 |
| 3,850,663 | 11/1974 | Hagenbach | 430/108 |
| 3,893,934 | 7/1975 | Braun et al. | 430/110 |
| 3,898,170 | 8/1975 | Kasper | 430/108 |
| 3,970,571 | 7/1976 | Olson et al. | 430/110 |
| 4,002,776 | 1/1977 | Braun et al. | 430/110 |
| 4,042,518 | 8/1977 | Jones | 430/108 |
| 4,076,857 | 2/1978 | Kasper et al. | 430/103 |
| 4,157,257 | 6/1979 | Takematsu et al. | 71/103 |
| 4,205,176 | 5/1980 | Zestermann et al. | 548/239 |
| 4,394,430 | 7/1983 | Jadwin et al. | 430/110 |
| 4,414,152 | 11/1983 | Santilli et al. | 430/114 |
| 4,416,965 | 11/1983 | Sandhu et al. | 430/109 |
| 4,478,925 | 10/1984 | Miskinis | 430/108 |
| 4,480,021 | 10/1984 | Lu et al. | 430/106.6 |
| 4,517,272 | 5/1985 | Jadwin et al. | 430/110 |
| 4,646,452 | 3/1987 | Gruber et al. | 430/110 |
| 4,684,596 | 8/1987 | Bonser et al. | 430/110 |
| 4,726,994 | 2/1988 | Yoerger | 430/137 |
| 4,758,491 | 7/1988 | Alexandrovich et al. | 430/110 |
| 5,157,156 | 10/1992 | Giordano et al. | 568/64 |
| 5,186,736 | 2/1993 | Ort et al. | 504/225 |
| 5,192,637 | 3/1993 | Saito et al. | 430/109 |

OTHER PUBLICATIONS

L.P. Hammett, *Chem. Revs.*, vol. 17, (1935), pp. 125–136.
Kemp & Steven, *J. Chem. Soc.*, vol. 11, (1948), pp. 110–112.
*J. Amer. Chem. Soc.*, vol. 75, (1953), p. 6326.
*J. Amer. Chem. Soc.*, vol. 64, (1942), p. 2763.
*Zh. Org. Khim.*, vol. 11, No. 1 (1975), p. 113.

*Primary Examiner*—Brian M. Burn
*Attorney, Agent, or Firm*—Robert Luke Walker; Anne B. Kiernan

[57] ABSTRACT

An electrophotographic toner having polymeric binder and a charge control agent selected from the group consisting of sulfonamides having the general structure:

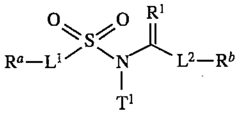

and metal salts thereof. $T^1$ is independently selected from H, alkyl having from 1 to 20 carbons, cycloalkyl having from 3 to 18 carbons, and aromatic and heteroaromatic ring systems having a solitary ring or 2 to 3 linked or fused rings. $R^1$ is O, S, N—H, N—$R^5$, or N—L—$R^5$; where L is a linking group selected from:

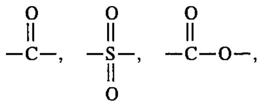

and 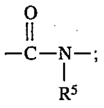

and $R^5$ is independently selected from alkyl having from 1 to 20 carbons, cycloalkyl having from 3 to 18 carbons, and aromatic and heteroaromatic ring systems having a solitary ring or 2 to 3 linked or fused rings. $L^1$ and $L^2$ are each independently a direct link or divalent alkyl or fluoroalkyl having from 1 to 20 carbons. $R^a$ and $R^b$ are each independently selected from the group consisting of H, F and ring systems having a solitary ring or from 2 to 3 fused or linked rings, said ring system having from 3 to 34 carbons, including carbons of substituent groups. If $L^1$ is a direct link, $R^a$ is a ring system and if $L^2$ is a direct link, $R^b$ is a ring system.

24 Claims, No Drawings

N-(CARBONYL, CARBONIMIDOYL, CARBONOTHIOYL)SULFONAMIDE CHARGE CONTROL AGENTS AND TONERS AND DEVELOPERS

This application is a divisional of Ser. No. 08/171,783 filed Dec. 22, 1993, now U.S. Pat. No. 5,405,727.

FIELD OF THE INVENTION

The invention relates to electrographic materials, particularly charge control agents, and toners and developers incorporating those agents. This invention more particularly relates to N-(carbonyl,carbonimidoyl,carbonothioyl)sulfonamide charge control agents and toners and developers including those agents.

BACKGROUND OF THE INVENTION

In electrography, image charge patterns are formed on a support and are developed by treatment with an electrographic developer containing marking particles which are attracted to the charge patterns. These particles are called toner particles or, collectively, toner. Two major types of developers, dry and liquid, are employed in the development of the charge patterns.

In electrostatography, the image charge pattern, also referred to as an electrostatic latent image; is formed on an insulative surface of an electrostatographic element by any of a variety of methods. For example, the electrostatic latent image may be formed electrophotographically, by imagewise photo-induced dissipation of the strength of portions of an electrostatic field of uniform strength previously formed on the surface of an electrophotographic element comprising a photoconductive layer and an electrically conductive substrate. Alternatively, the electrostatic latent image may be formed by direct electrical formation of an electrostatic field pattern on a surface of a dielectric material.

One well-known type of electrostatographic developer comprises a dry mixture of toner particles and carrier particles. Developers of this type are employed in cascade and magnetic brush electrostatographic development processes. The toner particles and carrier particles differ triboelectrically, such that during mixing to form the developer, the toner particles acquire a charge of one polarity and the carrier particles acquire a charge of the opposite polarity. The opposite charges cause the toner particles to cling to the carrier particles. During development, the electrostatic forces of the latent image, sometimes in combination with an additional applied field, attract the toner particles. The toner particles are pulled away from the carrier particles and become electrostatically attached, in imagewise relation, to the latent image bearing surface. The resultant toner image can then be fixed, by application of heat or other known methods, depending upon the nature of the toner image and the surface, or can be transferred to another surface and then fixed.

Toner particles often include charge control agents, which, desirably, provide high uniform net electrical charge to toner particles without reducing the adhesion of the toner to paper or other medium. Many types of positive charge control agents, materials which impart a positive charge to toner particles in a developer, have been used and are described in the published patent literature. In contrast, few negative charge control agents, materials which impart a negative charge to toner particles in a developer, are known.

Prior negative charge control agents have a variety of shortcomings. Many charge control agents are dark colored and cannot be readily used with pigmented toners, such as cyan, magenta, yellow, red, blue, and green. Some are highly toxic or produce highly toxic by-products. Some are highly sensitive to environmental conditions such as humidity. Some exhibit high throw-off or adverse triboelectric properties in some uses. Use of charge control agents requires a balancing of shortcomings and desired characteristics to meet a particular situation. There is thus a continuing need for negative charge control agents which have improved properties.

U.S. Pat. No. 4,480,021 teaches the use as negative charge control agents of sulfonamides and sulfones having the formula: $R_1—SO_2—R_2$ or $R_3—SO_2—NH—R_4$, in which $R_1$ is alkyl having from about 6 to about 22 carbons or aryl, $R_2$ is aryl having from about 6 to about 18 carbons, $R_3$ is aryl or alkyl group, and $R_4$ is alkyl, independent from $R_3$ having from about 6 to 22 carbons or aryl. Specific examples of aryl alkyl sulfonamides were named: para-tolyl stearyl sulfonamide, para-tolyl cetyl sulfonamide, para-xylyl stearyl sulfonamide, para-tolyl myristyl sulfonamide, and isopropyl biphenyl stearyl sulfonamide.

U.S. Pat. No. 4,464,452 teaches toner compositions including a negative charge control agent having the general structure:

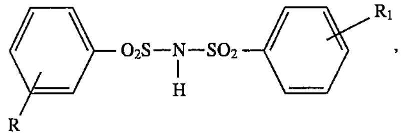

(1)

in which R and $R_1$ are selected from H, alkyl, halo, nitro, "and the like". This patent also teaches as specific examples of negative charge control agents: di-tolyl sulfonimide, phenyl tolyl sulfonimide, diphenyl sulfonimide, di-1-naphthyl sulfonimide, hexadecyl tolyl sulfonimide, methyl tolyl sulfonimide, and dihexadecyl sulfonimide.

U.S. Pat. No. 3,577,345 teaches toners and developers including a material having the general structure:

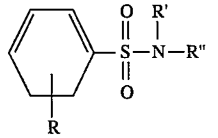

(2)

in which R is selected from H, Cl, Br, aryl, alkyl having from 1 to 6 carbons; R' and R" are selected from H, aryl having from 1 to 12 carbons and alkyl having from 1 to 12 carbons and chlorinated $Ph—(Ph)_n—Ph$ (n=0–3). This material is not used as a charge control agent, but rather as an additive for modifying toner melt and viscosity. Similar melt and viscosity modifying additives are taught in U.S. Pat. Nos. 3,893,934 and 4,002,776. Those additives have the general structure:

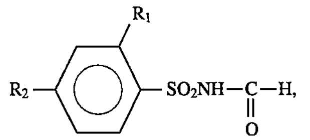

(3)

in which one of $R_1$ and $R_2$ is $CH_3$ and the other is H. These three patents do not teach or suggest whether these materials are capable of functioning as charge control agents for modification of charge. Charge control agents are commonly used in the range of about 0.5 to 3.0 weight percent. The melt and viscosity additives, in these patents have concentrations in toners in the range of about 10 to 40 weight percent.

U.S. Pat. No. 5,186,736 to Ong et al teaches toners having charge control additives having the general structure

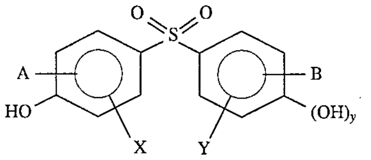

where A and B are independently selected from hydrogen, alkyl, alkoxy, carboxy, nitro, and halogen and X and Y are independently selected from hydrogen, hydroxy, alkyl, alkoxy, carboxy, nitro, and halogen and y is 0 or 1.

U.S. Pat. No. 5,186,736 to Ort et al teaches heterocyclic N-acylsulfonamide herbicides or growth regulators having the general structure:

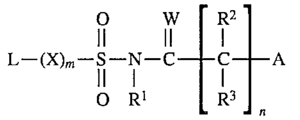

where $R^1$ is H or an aliphatic radical; $R^2$ and $R^3$ are H, alkyl or phenyl; W is O, S, $NR^4$ or $NOR^4$; X is $CHR^2$, O or $NR^4$; L is a (substituted) phenyl, napthyl, or monocyclic heteroaryl radical; A is a (substituted) pyrimidyl, triazinyl, triazolyl or bicyclic heteroaryl radical; $R^4$ is H, $C_1$–$C_3$-alkyl, $C_1$–$C_3$-haloalkyl, or phenyl; and m and n are 0 or 1.

SUMMARY OF THE INVENTION

The invention, in its broader aspects, provides an electrophotographic toner having polymeric binder and a charge control agent selected from the group consisting of sulfonamides having the general structure:

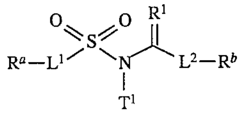

and metal salts thereof. $T^1$ is independently selected from H, alkyl having from 1 to 20 carbons, cycloalkyl having from 3 to 18 carbons, and aromatic and heteroaromatic ring systems having a solitary ring or 2 to 3 linked or fused rings. $R^1$ is O, S, N—H, N—$R^5$, or N—L—$R^5$; where L is a linking group selected from:

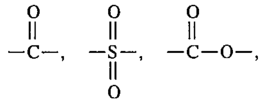 and 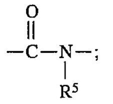;

and $R^5$ is independently selected from alkyl having from 1 to 20 carbons, cycloalkyl having from 3 to 18 carbons, and aromatic and heteroaromatic ring systems having a solitary ring or 2 to 3 linked or fused rings. $L^1$ and $L^2$ are each independently a direct link or divalent alkyl or fluoroalkyl having from 1 to 20 carbons. $R^a$ and $R^b$ are each independently selected from the group consisting of H, F and ring systems having a solitary ring or from 2 to 3 fused or linked rings, said ring system having from 3 to 34 carbons, including carbons of substituent groups. If $L^1$ is a direct link, $R^a$ is a ring system and if $L^2$ is a direct link, $R^b$ is a ring system.

It is an advantageous effect of at least some of the embodiments of the invention that negatively charging toners can be provided which have favorable charging characteristics.

DESCRIPTION OF PARTICULAR EMBODIMENTS

The term "particle size" used herein, or the term "size", or "sized" as employed herein in reference to the term "particles", means the median volume weighted diameter as measured by conventional diameter measuring devices, such as a Coulter Multisizer, sold by Coulter, Inc of Hialeah, Fla. Median volume weighted diameter is the diameter of an equivalent weight spherical particle which represents the median for a sample; that is, half of the mass of the sample is composed of smaller particles, and half of the mass of the sample is composed of larger particles than the median volume weighted diameter.

The term "charge control" refers to a propensity of a toner addenda to modify the triboelectric charging properties of the resulting toner.

The term "glass transition temperature" or "Tg" as used herein means the temperature at which a polymer changes from a glassy state to a rubbery state. This temperature (Tg) can be measured by differential thermal analysis as disclosed in "Techniques and Methods of Polymer Evaluation", Vol. 1, Marcel Dekker, Inc., New York, 1966.

The sulfonamides of the invention, which are useful as charge control agents in electrophotographic toners, can be represented by the general structure:

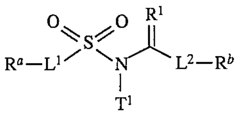 (4)

or the general structure:

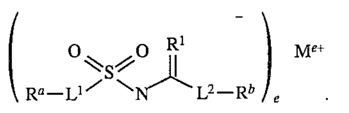 (5)

All designations are defined below. The sulfonamides of the invention generally can tautomerize, thus structure (4), for example; could, in many cases, also be represented:

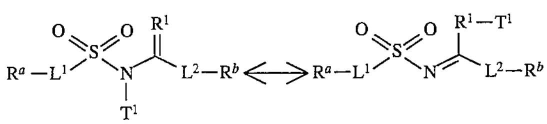 (6)

For the sake of brevity, alternate tautomeric forms will not be illustrated herein, however, structural formulas should be understood to be inclusive of alternate tautomers. For example, the amido form of the following sulfonamide of the invention:

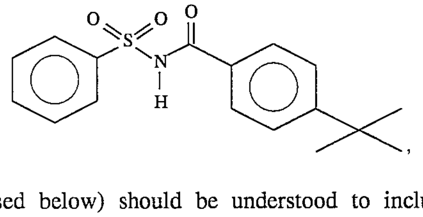, (discussed below) should be understood to include the iminol form:

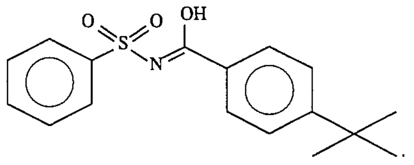

In all structural formulas herein, identical designations, for example: "$R^1$" have the same meaning in all formulas, unless a more narrow definition is specifically indicated.

Compounds represented by formula (5) are salts of a metal "M" selected from: Na, Mg, and K. The metal has a valence "e" of 1 or 2. Specific examples of these materials are provided in Examples AP, AQ, and AR. The sulfonamide metal salts of the invention are not currently preferred for use as charge control agents because toner containing these materials exhibited undesirably low charge levels.

$T^1$ is selected from H; alkyl having from 1 to 20 carbons, cycloalkyl having from 3 to 18 carbons, and aromatic and heteroaromatic ring systems having a solitary ring or 2 to 3, linked or fused rings. The alkyl or ring system can be unsubstituted or can be substituted with the groups described below in relation to $R^a$ and $R^b$.

Sulfonamides of the invention in which $T^1$ is not H, have, been determined to, surprisingly, be non-preferred for use as charge control agents because of high throw-off and poor charge control. Specific examples of such sulfonamides are provided in Examples AS, AT, and AU. When $T^1$ is H, general structure (4) reduces to:

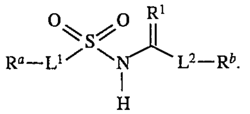

(7)

In general structures (4), (5), and (6); $R^1$is S, O, or $NT^2$. The respective materials can be designated: for $R^1$=O: N-(carbonyl)-(alkyl or aryl)sulfonamides; for $R^1$=S: N-((alkyl or aryl)sulfonyl)-carbothioamides or N-(cabonothioyl)-(alkyl or aryl)sulfonamides; and for $R^1$=$NT^2$: N-((alkyl or aryl)sulfonyl)-carboximidamides or N-(carbonimidoyl)-(alkyl or aryl)sulfonamides.

$T^2$ represents H, $R^5$ or -L-$R^5$ where $R^5$ is selected from alkyl having from 1 to 20 carbons, cycloalkyl having from 3 to 18 carbons, and aromatic and heteroaromatic ring systems having a single ring or from 2 to 3 linked or fused rings. The alkyl group or ring system can be unsubstituted or can be substituted with the groups described below in relation to $R^a$ and $R^b$. L is a linking group selected from:

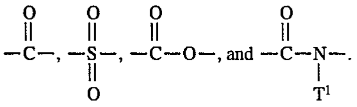

$R^1$=S or O is currently preferred over $NT^2$ and O is currently preferred over S for use as charge control agents. Sulfonamides of the invention having the general structure:

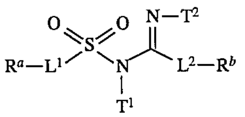

(8)

are thus not currently preferred. Examples of specific such sulfonamides are provided in Examples AV, AX, AY, AZ, and BA. Sulfonamides of the invention, which have the general structure:

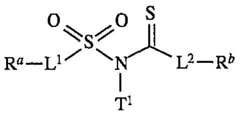

(9)

are not currently as highly preferred as are sulfonamides of the invention in which $R^1$ is O. Specific examples of sulfonamides in which $R^1$=S are the N-(phenylsulfonyl)-carbothiobenzamides illustrated by Examples BB and BC.

Taking into account the preferred groups for $T^1$ and $R^1$ reduces general structure (4) to:

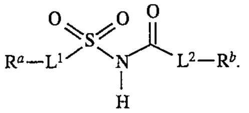

(10)

In the sulfonamides of the invention, $R^a$ and $R^b$ are each independently selected from H or a ring system having a solitary ring or 2 or 3 fused or linked rings. $L^1$ and $L^2$ are each independently a direct link or divalent alkyl or fluoroalkyl having from 1 to 20 carbons. If $L^1$ or $L^2$ is a direct link, $R^a$ or $R^b$, respectively, is a ring system or alkyl rather than H.

Each $R^a$ or $R^b$ ring system is cycloalkyl, aromatic, or heteroaromatic and has from 3 to 34 carbons counting carbons of any substituent group or groups. In most of the specific examples described herein, $R^a$ and $R^b$ are phenyl, however, non-phenyl $R^a$ and $R^b$ aromatic groups are not currently disfavored. An example of a sulfonamide in which $R^a$ is a fused ring system is presented in Examples F1 and F2.

$R^a$ and $R^b$ groups, when a ring system, can be unsubstituted or can have one or more substituents selected from the group: alkyl having from 1 to 20 carbons, $NO_2$, $NH_2$, OH, COOH, cycloalkyl having from 3 to 6 carbons, halo, alkoxy having from 1 to 20 carbons, alkycarbonyloxy having from 2 to 20 carbons and carboalkoxy having from 2 to 20 carbons.

Sulfonamides of the invention, in which $R^a$—$L^1$— and —$L^2$—$R^b$ are either or both alkyl are not currently preferred as charge control agents. Examples of embodiments of such materials are compounds having the general structures:

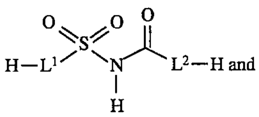

and

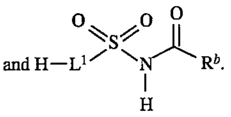

(11) (12)

Specific examples of these sulfonamides are presented in Examples BG and BH.

In embodiments of the sulfonamides of the invention, preferred for use as charge control agents, neither $R^a$ nor $R^b$ is H and $L^1$ and $L^2$ may or may not be direct links. In a number of embodiments of the invention, $L^1$ and $L^2$ are both direct links and general structure (10) reduces to:

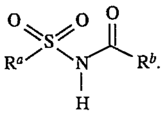

(13)

These materials can be referred to as N-(carbonyl)-arylsulfonamides or N-aroylarylsulfonamides.

It is desirable that in the sulfonamides of the invention, $R^a$ or $R^b$ or both are phenyl and are substituted with one or more tertiary alkyl or tertiary fluoroalkyl groups having from 4 to 8 carbons. Examples of specific t-alkyl substituted sulfonamides include Examples A–G, I–M, Q–Y, Z.A–Z.E, AA–AP, AX–AY, BA–BC, and BH. In the more desirable of these Examples; A–G, I–M, Q–X, and AA–AO.B; $R^a$ and $R^b$ are both phenyl, $R^1$ is O, $T^1$ is H and that the t-alkyl is t-butyl. Linear alkyl substituted materials, for example, the material of Example H, are not presently preferred for use as charge control agents.

In a more desirable embodiment of the sulfonamides of the invention, $R^a$ and $R^b$ are phenyl and one of $R^a$ and $R^b$ is substituted with a tertiary alkyl group having from 4 to 8 carbons and the other ring is substituted with an electron withdrawing group, preferably $NO_2$, Cl, Br, F, CN, $CO_2R^x$ (where $R^x$ is alkyl having from 1 to 20 carbons), $CF_3$, or $SO_2CH_3$. Specific examples of these materials include Examples I–L and Q–W. In contrast, it is not preferred to have only electron withdrawing substituents. This is demonstrated in Examples N–P.

Especially preferred are materials in which $R^a$ and $R^b$ are aryl and which are substituted with two t-alkyl or t-fluoroalkyl groups on one of $R^a$ and $R^b$ and one or two electron withdrawing groups on the other. Currently preferred are phenyl $R^a$ and $R^b$ groups. Specific examples includes Examples Q–W. Suitable electron withdrawing groups for this embodiment, may be selected on the basis of positive Hammett Sigma values, which represent a measure of the electronegativity of a substituent relative to the unsubstituted derivative (where substituent=H). (L. P. Hammett, Chem. Revs., Vol. 17, p. 125 et seq, (1935)) A Hammett Substituent value is defined relative to benzoic acid. By definition, for benzoic acids: sigma=log K–log K°, where K is the ionization constant for a substituted benzoic acid in water at 25° C. and K° is the ionization constant for benzoic acid. $\sigma$ is zero for H. Substituents with a $\sigma$ greater than zero are more electronegative than H. Substituents with a $\sigma$ less than zero are less electronegative than H. Hammett substituent values are problematic for ortho substituents. Hammett substituent values may or may not be additive for multiple substituents on a single ring. Examples of Hammett Sigma values are presented in Table 1.

TABLE 1

| Substituent | Hammett Sigma |
|---|---|
| para-$NH_2$ | −0.57 |
| para-$OCH_3$ | −0.28 |
| para-tert-butyl | −0.15 |
| para-$CH_3$ | −0.14 |
| H | 0.00 |
| meta-$OCH_3$ | +0.10 |
| para-Cl | +0.24 |
| meta-Cl | +0.37 |
| para-$COOCH_3$ | +0.44 |
| para-COOH | +0.44 |
| meta-$NO_2$ | +0.71 |
| para-$NO_2$ | +0.81 |

Not preferred are sulfonamides of the invention having two electron withdrawing groups on one ring and a single t-alkyl group on the other ring, such as the sulfonamide of Example Y or having single substituents of about the same electronegativity on each ring, as in Examples Z, C, and N.

Another preferred embodiment of the invention can be represented by general structure (7):

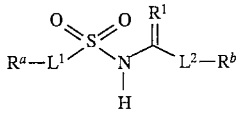

(7)

with the limitation that: $R^1$, $L^1$, $L^2$, have the same meanings as above discussed; but $R^a$ and $R^b$ are both aromatic ring systems and at least one of $R^a$ and $R^b$ is a phenyl moiety having two t-butyl substituents and a third substituent.

In one particular embodiment, $R^a$ or $R^b$ is the moiety:

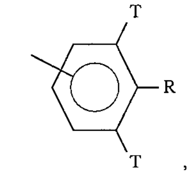

, where T is tertiary alkyl having from 4 to 8 carbons; and R is an electron donating group. Suitable R groups include OH, $NH_2$, $N(CH_3)_2$, alkyl having from 1 to 8 carbons, and alkoxy having from 1 to 8 carbons. Branched and other relatively large R groups are not currently most preferred. Currently most preferred is an embodiment in which $R^a$ or $R^b$ is a phenyl substituted with two meta t-alkyl groups and a para OH group. The currently preferred t-alkyl groups are tert-butyl.

In another embodiment, $R^a$ or $R^b$ is the moiety:

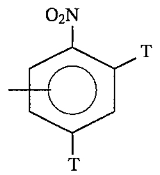

T is tertiary alkyl having from 4 to 8 carbons and is preferably tert-butyl.

In both of these embodiments, the other one of $R^a$ and $R^b$ is unsubstituted; or is substituted with two meta t-alkyls and a para OH; or is substituted by one or more other substituents. Suitable substituents, in this embodiment, can be electron withdrawing or electron donating. Examples of suitable substituents include: alkyl having from 1 to 20 carbons, $NO_2$, $NH_2$, OH, COOH, cycloalkyl having from 3 to 6 carbons, halo, alkoxy having from 1 to 20 carbons, and alkycarbonyloxy having from 2 to 20 carbons or carboalkoxy having from 2 to 20 carbons.

Specific examples of sulfonamides of this embodiment of the invention are provided in the Examples: in Example AA, $L^1$ is a direct link, $R^a$ and $R^b$ are phenyls, and $R^b$ is substituted with two meta t-alkyl groups and a para OH group; in Examples AB–AN, $L^1$ and $L^2$ are both direct links, and $R^a$ and $R^b$ are each phenyl ring systems.

The following reaction scheme illustrates the preparation of sulfonamides of the invention. The example sulfonamide prepared in this scheme is N-(4-nitrobenzoyl)-4-t-butylbenzenesulfonamide:

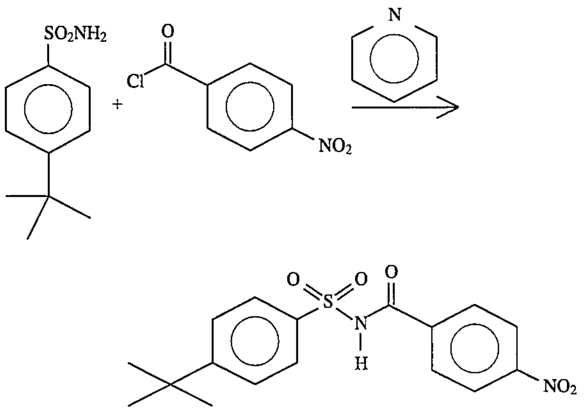

This scheme follows a general method disclosed in Kemp and Stephen, J. Chem. Soc., 1948, 11. Aromatic sulfonamide was acylated with an acid chloride in the presence of a 100 percent stoichiometric excess of pyridine. Equivalent procedures substituting appropriate starting materials can be followed for the other sulfonamides of the invention, with the following exceptions.

N-Arylsulfonylarylcarboximidamides and N-arylsulfonylarylcarbothioamides can be produced from N-aroylarylsulfonamides by the following reaction scheme:

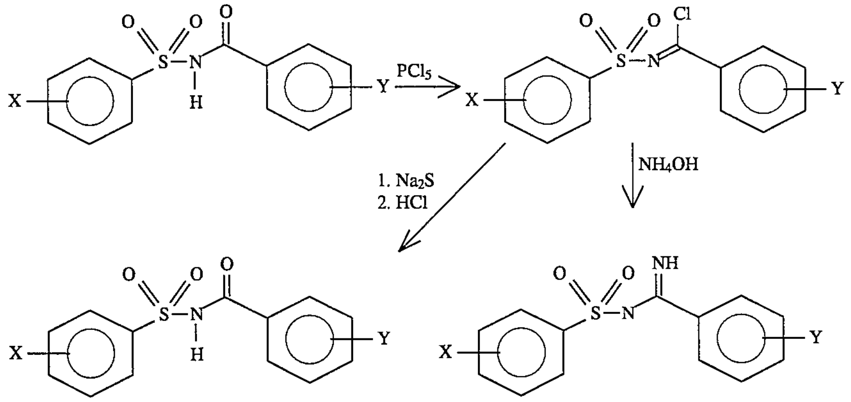

The following reaction scheme illustrates the preparation of N-(3,5-di-t-butyl-4-hydroxybenzoyl)benzenesulfonamide and other di-t-butyl-hydroxy substituted sulfonamides:

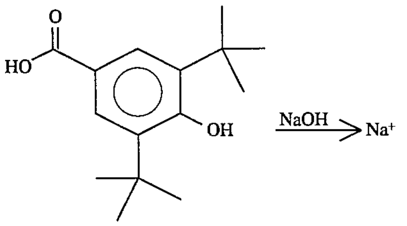

-continued

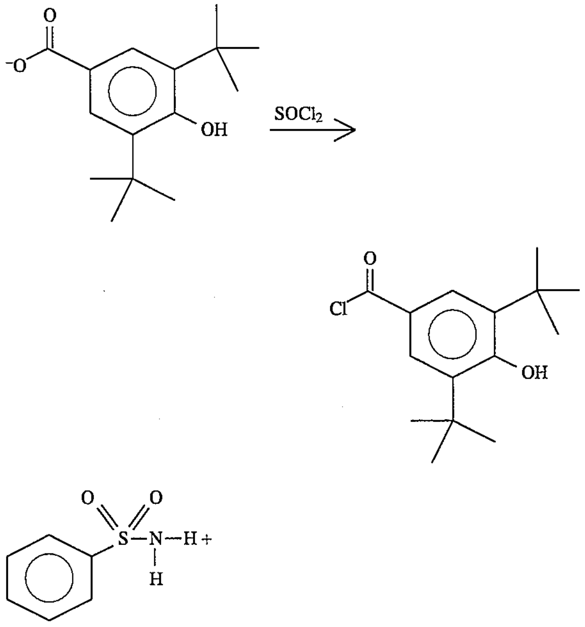

-continued

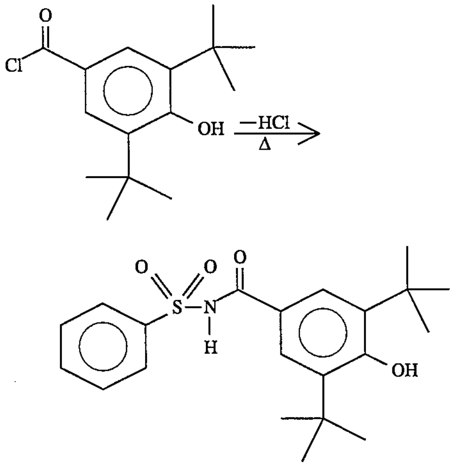

The following two reaction schemes can be utilized, in appropriate examples, where the hydroxyl group is replaced by an acetoxy or the like:

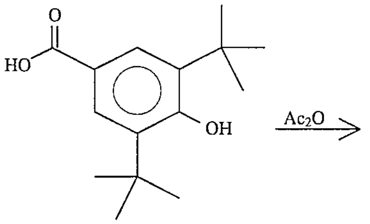

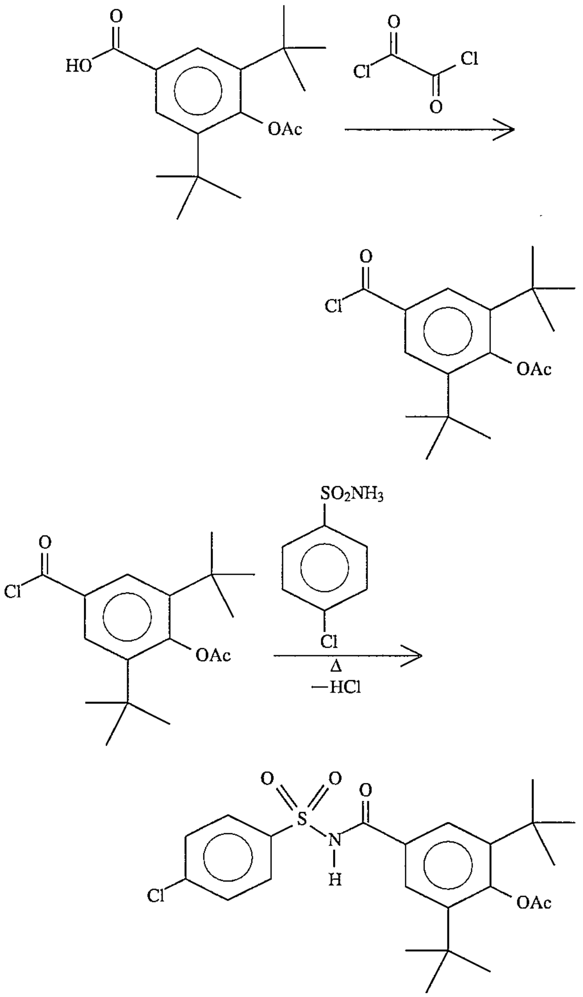

Other sulfonamides, differing from those claimed herein, are described in U.S. patent application Ser. No. 08/316,006, (now U.S. Pat. No. 5,523,484) entitled: "BIS AND TRIS N-(CARBONYL,CARBONIMIDOYL,CARBONOTHIOYL)SULFONAMIDE CHARGE CONTROL AGENTS, TONERS AND DEVELOPERS", filed Dec. 9, 1994 by inventors: John C. Wilson and Peter S. Alexandrovich, the disclosure of which is hereby incorporated by reference.

The toner of the invention includes charge control agent of the invention, in an amount effective to modify, and preferably, improve the properties of the toner. It is preferred that a charge control agent improve the charging characteristics of a toner, so the toner quickly charges to a negative value having a relatively large absolute magnitude and then maintains about the same level of charge. Relatively large values of charge per mass that are currently preferred are in the 25–35 microcoloumbs/gram range. Exceeding the upper end of the range can result in low density on copy, and is thus not preferred. The sulfonamides of the invention are negative charge control agents, thus the toners of the invention, it is preferred, achieve and maintain negative charges having relatively large absolute magnitudes.

It is also preferred that a charge control agent improve the charge uniformity of a toner composition, that is, they insure that substantially all of the individual toner particles exhibit a triboelectric charge of the same sign with respect to a given carrier. It is also preferred that toner throw-off be minimized. The term "toner throw-off" refers to the amount of toner powder thrown out of a developer mix as it is mechanically agitated, for example, within a development apparatus. Throw-off can cause unwanted background development and general contamination problems. It is further preferred that the charge control agent used in a toner not be phase separated within the toner (at least in so far as phase separation visible in toner melted onto a glass slide under a microscope at 650 times magnification). It has been determined empirically that such phase separation can correlate with increased clumping of the toner powder, and can lead to irreproducible manufacture of toner. It is also preferred that a charge control agent be colorless, particularly for use in light colored toners. The charge control agents of the invention are colorless, with the exception of those in which $R^1$=S. It is also preferred that a charge control agent be metal free and have good thermal stability. The charge control agents of the preferred embodiments of the invention are metal free and have good thermal stability. Preferred materials described herein are based upon an evaluation in terms of a combination of characteristics rather than any single characteristic.

The properties of the thermoplastic polymers employed as the toner matrix phase in the present invention can vary widely. Typically, and preferably, amorphous toner polymers having a glass transition temperature in the range of about 50° C. to about 120° C. or blends of substantially amorphous polymers with substantially crystalline polymers having a melting temperature in the range of about 65° C. to about 200° C. are utilized in the present invention. Preferably, such polymers have a molecular weight distribution including an insoluble, very high molecular weight fraction and one or more fractions having a number average molecular weight in the range of about 1000 to about 500,000 and a weight average molecular weight in the range of about $2\times10^3$ to about $3\times10^6$. Preferably, the thermoplastic polymers used in the practice of this invention are substantially amorphous. However, as indicated above, mixtures of polymers can be employed, if desired, such as mixtures of substantially amorphous polymers with substantially crystalline polymers.

Polymers useful as binders in the toner of the invention include styrenic/acrylic copolymers. In general, preferred styrenic/acrylic copolymers have a glass transition temperature in the range of about 50° C. to about 100° C. In a particular embodiment of the invention, the resin is a copolymer of styrene and butyl acrylate, crosslinked with divinyl benzene; produced in a suspension or emulsion polymerization process. An initiator and, optionally, a chain transfer agent are used in the synthesis. The ratio of styrene to butyl acrylate is in the range of from 90:10 to 60:40 and the divinyl benzene is used at a level of 3 weight percent or less, preferably, at a level of about 0.1 to 1.0 weight percent.

An optional but preferred component of the toner of the invention is colorant: a pigment or dye. Suitable dyes and pigments are disclosed, for example, in U.S. Reissue Patent No. 31,072 and in U.S. Pat. Nos. 4,160,644; 4,416,965; 4,414,152; and 2,229,513. One particularly useful colorant for toners to be used in black and white electrostatographic copying machines and printers is carbon black. Colorants are generally employed in the range of from about 1 to about 30 weight percent on a total toner powder weight basis, and preferably in the range of about 2 to about 15 weight percent.

The toner of the invention can also contain other additives of the type used in previous toners, including leveling agents, surfactants, stabilizers, and the like. The total quantity of such additives can vary. A present preference is to employ not more than about 10 weight percent of such additives on a total toner powder composition weight basis.

Dry styrenic/acrylic copolymer toners of this invention can optionally incorporate a small quantity of low surface energy material, as described in U.S. Pat. Nos. 4,517,272 and 4,758,491. Optionally the toner can contain a particulate additive on its surface such as the particulate additive disclosed in U.S. Pat. No. 5,192,637.

The charge control agent is incorporated into the toner. For example, in a dry electrostatographic toner, the charge control agent of the invention can be mixed in any convenient manner, such as blending in the manner described in U.S. Pat. Nos. 4,684,596 and 4,394,430, with an appropriate polymeric binder material and any other desired addenda. The mixture is then ground to desired particle size to form a free-flowing powder of toner particles containing the charge agent.

A preformed mechanical blend of particulate polymer particles, charge control agent, colorants and additives can, alternatively, be roll milled or extruded at a temperature sufficient to melt blend the polymer or mixture of polymers to achieve a uniformly blended composition. The resulting material, after cooling, can be ground and classified, if desired, to achieve a desired toner powder size and size distribution. For a polymer having a $T_g$ in the range of about 50° C. to about 120° C., or a $T_m$ in the range of about 65° C. to about 200° C., a melt blending temperature in the range of about 90° C. to about 240° C. is suitable using a roll mill or extruder. Melt blending times, that is, the exposure period for melt blending at elevated temperature, are in the range of about 1 to about 60 minutes. After melt blending and cooling, the composition can be stored before being ground. Grinding can be carried out by any convenient procedure. For example, the solid composition can be crushed and then ground using, for example, a fluid energy or jet mill, such as described in U.S. Pat. No. 4,089,472. Classification can be accomplished using one or two steps.

In place of melt blending or the like, the polymer can be dissolved in a solvent in which the charge control agent and other additives are also dissolved or are dispersed. The resulting solution can be spray dried to produce particulate toner powders. Limited coalescence polymer suspension procedures as disclosed in U.S. Pat. No. 4,833,060 are particularly useful for producing small sized, uniform toner particles.

The toner particles have an average diameter between about 0.1 micrometers and about 100 micrometers, and desirably have an average diameter in the range of from about 4 micrometers to 30 micrometers for currently used electrostatographic processes. The size of the toner particles is believed to be relatively unimportant from the standpoint of the present invention; rather the exact size and size distribution is influenced by the end use application intended. So far as is now known, the toner particles can be used in all known electrostatographic copying processes.

The developers of the invention include carrier and toner of the invention. Carriers can be conductive, non-conductive, magnetic, or non-magnetic. Carriers are particulate and can be glass beads; crystals of inorganic salts such as aluminum potassium chloride, ammonium chloride, or sodium nitrate; granules of zirconia, silicon, or silica; particles of hard resin such as poly(methyl methacrylate); and particles of elemental metal or alloy or oxide such as iron, steel, nickel, carborundum, cobalt, oxidized iron and mixtures of such materials. Examples of carriers are disclosed in U.S. Pat. Nos. 3,850,663 and 3,970,571. Especially useful in magnetic brush development procedures are iron particles such as porous iron, particles having oxidized surfaces, steel particles, and other "hard" and "soft" ferromagnetic materials such as gamma ferric oxides or ferrites of barium, strontium, lead, magnesium, or aluminum. Such carriers are disclosed in U.S. Pat. Nos. 4,042,518; 4,478,925; and 4,546,060.

Carrier particles can be uncoated or can be coated with a thin layer of a film-forming resin to establish the correct triboelectric relationship and charge level with the toner employed. Examples of suitable resins are the polymers described in U.S. Pat. Nos. 3,547,822; 3,632,512; 3,795,618 and 3,898,170 and Belgian Patent No. 797,132. Other useful resins are fluorocarbons such as polytetrafluoroethylene, poly(vinylidene fluoride), mixtures of these, and copolymers of vinylidene fluoride and tetrafluoroethylene. See for example, U.S. Pat. Nos. 4,545,060; 4,478,925; 4,076,857; and 3,970,571. Polymeric fluorocarbon coatings can aid the developer to meet the electrostatic force requirements mentioned above by shifting the carrier particles to a position in the triboelectric series different from that of the uncoated carrier core material to adjust the degree of triboelectric charging of both the carrier and toner particles. The polymeric fluorocarbon coatings can also reduce the frictional characteristics of the carrier particles in order to improve developer flow properties; reduce the surface hardness of the carrier particles to reduce carrier particle breakage and abrasion on the photoconductor and other components; reduce the tendency of toner particles or other materials to undesirably permanently adhere to carrier particles; and alter electrical resistance of the carrier particles.

In a preferred embodiment of the invention, the carrier is strontium ferrite coated with poly(methyl methacrylate) (PMMA) on a 2 percent weight/weight basis or strontium ferrite coated with dehydrofluorinated and oxidized fluorocarbon as disclosed in U.S. Pat. No. 4,726,994, the specification of which is hereby incorporated by reference herein. The fluorocarbon is coated on a 0.5 percent weight/weight basis. The fluorocarbon carrier is also referred to herein as "modified Kynar".

In a particular embodiment, the developer of the invention contains from about 1 to about 20 percent by weight of toner of the invention and from about 80 to about 99 percent by weight of carrier particles. Usually, carrier particles are larger than toner particles. Conventional carrier particles have a particle size of from about 5 to about 1200 micrometers and are generally from 20 to 200 micrometers.

The toners of the invention are not limited to developers which have carrier and toner, and can be used, without carrier, as single component developer.

The toner and developer of the invention can be used in a variety of ways to develop electrostatic charge patterns or latent images. Such developable charge patterns can be prepared by a number of methods and are then carried by a suitable element. The charge pattern can be carried, for example, on a light sensitive photoconductive element or a non-light-sensitive dielectric surface element, such as an insulator coated conductive sheet. One suitable development technique involves cascading developer across the electrostatic charge pattern. Another technique involves applying toner particles from a magnetic brush. This technique involves the use of magnetically attractable carrier cores. After imagewise deposition of the toner particles the image can be fixed, for example, by heating the toner to cause it to fuse to the substrate carrying the toner. If desired, the unfused image can be transferred to a receiver such as a blank sheet of copy paper and then fused to form a permanent image.

The invention is further illustrated by the following Examples and Comparative Examples. Unless otherwise indicated, all starting materials were commercially obtained. All melting points in the Examples and Comparative Examples are uncorrected. Nuclear magnetic resonance (NMR) spectra were obtained in $CDCl_3$ or dimethylsulfoxide-$d_6$ with a Varian Gemini-200 NMR spectrometer, marketed by Varian Associates, of Palo Alto, Calif. Elemental analyses were performed by combustion techniques, unless otherwise indicated and with the exception that metal analyses and bromine analyses were performed by neutron activation techniques. Thermogravimetric analyses were obtained with a Perkin-Elmer 7 series Thermal Analysis System at a heating rate of 10° C./min in air from 75°–400° C. Results are generally only reported here for colorless toners. Both black and blue toners were prepared for many of the sulfonamide charge control agents described herein, and results were in all cases, comparable to results with colorless toners.

In the Examples, a letter followed by a 1 designates a developer which includes PMMA coated carrier and a letter followed by a 2 designates a developer which includes a modified Kynar coated carrier. Letter designations in the Examples and Comparative Examples, correspond to similar letter designations of structural formulas. In Tables 2–19, "Ex" and "Com Ex" are the Example number or Comparative Example number, respectively; "CCA" is the designation of the structural formula of the charge control agent; "m.p." is melting point; "Conc"0 is the concentration of charge agent in styrene/n-butyl acrylate/divinylbenzene binder resin, expressed in parts per hundred parts of binder resin ("pph"), or weight percent ("wgt %"), as indicated; "P/S" is the visible phase separation at 650X; "2 min" and "10 min" are the charge to mass ratios (Q/m) in microcoloumbs/gram at the indicated times; "bich" indicates simultaneous positive and negative charging; and "T.O. (mg admix)" is throw-off in milligrams.

EXAMPLES

Examples A1, A2

Preparation of charge control agent

Sulfonamide charge control agent having the structural formula:

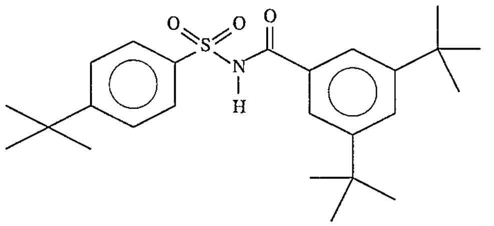

(A)

was prepared as follows. A mixture of 85.32 g (0.40 mol) of 4-t-butylbenzenesulfonamide, 101.12 g (0.40 mol) of 3,5-t-butylbenzoyl chloride and 63.28 g (0.80 mol) of pyridine was heated on a steam bath for 1.5 hours and cooled. The reaction mixture was dissolved in 1 liter of methylene chloride, washed 3 times with dilute HCl and once with water. The solution was dried over magnesium sulfate and concentrated. The residue was recrystallized from 3 liters of ethanol, collected, washed with ethanol and dried to give 118.2 grams (68.8% of theoretical yield) of product. The melting point for the product was determined to be 232°–234° C. Thermogravimetric analysis showed the product to be stable to 257° C.

A repetition of the above procedure yielded product having a melting point of 231°–232° C. Elemental analysis of that product gave: C=69.98, H=8.13, N=3.20, S=7.29. This compares to theoretical values of C=69.89, H=8.21, N=3.26, S=7.46. Nuclear magnetic resonance (NMR) in deuterated chloroform was conducted and supported the above-indicated structural formula for the product.

Preparation of colorless toners

A dry blend of 50.0 grams of poly(styrene-co-butyl acrylate-co-divinylbenzene) and 0.5 grams of the sulfonamide charge control agent A (structural formula A) was added to a heated two-roll compounding mill. The roller surfaces were set to 150° C. The melt was exercised on the mill for 20 minutes, then was removed and cooled. The resulting slab was first coarse ground to 2 mm size on a laboratory mill, then finely pulverized to approximately 12 micrometer size on a Trost TX jet mill. The toner thus prepared had a concentration of charge control agent of 1 part per hundred parts of styrene/n-butyl acrylate/divinylbenzene binder resin. This procedure was repeated, varying the concentration of charge control agent to provide concentrations of 2 and 4 parts per hundred (pph), on the same basis.

Preparation of black toners

The same procedures were followed as in the preparation of colorless toner having 1, 2, and 4 pph of charge control agent A, with the exception that 3.0 grams of Regal 300™ carbon black, marketed by Cabot Corp., was added to the dry blend placed in the compounding mill and the slab produced was initially coarse ground to 2 mm size, before being finely pulverized.

Preparation of blue toners

The same procedures were followed as in the preparation of colorless toner having 1, 2, and 4 pph charge control agent A, with the exception that 5 parts per hundred or copper phthalocyanine blue pigment from BASF Corp., was added to the dry blend placed in the compounding mill and the slab produced was initially coarse ground to 2 mm size, before being finely pulverized.

Preparation of developers-PMMA coated carrier

Developer was prepared for each of the toners indicated above, by mixing toner particles prepared as described above at a weight concentration of 12% toner with carrier particles comprising strontium ferrite cores thinly coated (approximately 2 percent by weight) with poly(methyl methacrylate). The volume average particle size of the carrier particles was from about 25 to 35 micrometers.

Preparation of developers-modified Kynar coated carrier

Developer was prepared for each of the toners indicated above, by mixing toner particles prepared as described above at a weight concentration of 12% toner with carrier particles comprising strontium ferrite cores thinly coated (approximately 0.5 percent weight/weight) with dehydrofluorinated and oxidized fluorocarbon as disclosed in U.S. Pat. No. 4,726,994. The volume average particle size of the carrier particles was from about 25 to 35 micrometers.

Evaluation of phase separation

Colorless toners were smear melted onto microscope slides at 180° C. and were examined microscopically at 650× magnification for evidence of phase separation.

Evaluation of toner charging

Toner charge was then measured in microcoulombs per gram of toner (μc/g) in a "MECCA" device. Prior to measuring the toner charge, the developer was vigorously shaken or "exercised" to cause triboelectric charging by placing a 4 gram sample of the developer into a plastic vial, capping the vial and shaking the vial on a "wrist-action" robot shaker operated at about 2 Hertz and an overall amplitude of about 11 cm for 2 minutes. Toner charge level after shaking was measured for each sample by placing a 100 milligram sample of the charged developer in a MECCA apparatus and measuring the charge and mass of transferred toner in the MECCA apparatus. This involves placing the 100 milligram sample of the charged developer in a sample dish situated between electrode plates and subjecting it, simultaneously for 30 seconds, to a 60 Hz magnetic field and an electric field of about 2000 volts/cm between the plates. The toner is released from the carrier and is attracted to and collects on the plate having polarity opposite to the toner charge. The total toner charge is measured by an electrometer connected to the plate, and that value is divided by the weight of the toner on the plate to yield the charge per mass of toner (Q/m). The toner charge level (i.e., charge-to-mass ratio) was also taken after exercising the developer for an additional 10 minutes by placing the magnetized developer in a glass bottle on top of a cylindrical roll with rotating magnetic core rotating at 2000 revolutions per minute. The magnetic core had 12 magnetic poles arranged around its periphery, in an alternating north and south fashion. This closely approximates typical actual usage of the developer in an electrostatographic development process. After this additional 10 minute exercising, the toner charge was measured in a MECCA apparatus. Values are reported in Tables 2–3 as Q/m 2 min. and 10 min.

Evaluation of throw-off

Throw-off values (T.O.) were determined by taking the 4 gram developer sample at 12% toner concentration that had been exercised for 10 minutes (following the 2 minute exercising), admixing in 6% more toner to provide a final toner concentration of about 18%), followed by 2 minutes more exercise on the wrist action shaker. This developer was then placed on a roll containing a rotating magnetic core, similar to a magnetic brush roll used for electrostatic development. A Plexiglas housing contained the assembly, and had a vacuum filter funnel mounted directly over the roll. The weight of toner, in milligrams, collected on a piece of filter paper after one minute of running the magnetic core at 2000 revolutions per minute was reported as the throw-off value.

Results are presented in Tables 2–3.

EXAMPLES B1,B2-Z1,Z2

The same procedures were substantially followed as described in Examples A1–A2, except the following. In Examples F1–F2, G1–G2, N1–N2, Q1–Q2, T1– T2, and W1–W2 tetrahydrofuran was added to the reaction mixture. In Examples V1–V2, charge control agent having structural formula (V) was prepared by permanganate oxidation of charge control agent having structural formula (E). In Examples X1–X2, charge control agent having structural formula (X) was prepared by catalytic reduction (high pressure hydrogenation) of charge control agent having structural formula Q.

Only colorless toners were produced. Results are presented in Tables 2–3. Sulfonamide charge control agents utilized in these examples are shown in the following structural formulas:

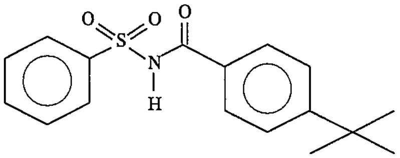
(B)

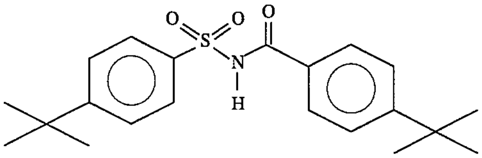
(C)

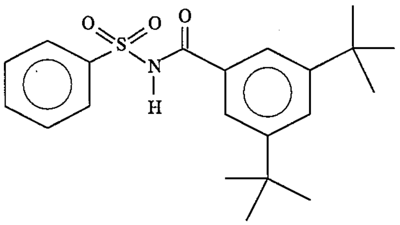
(D)

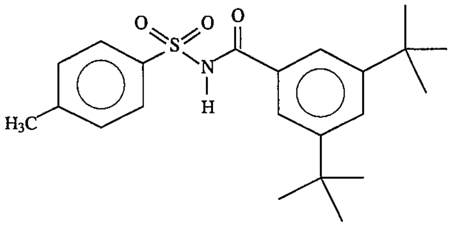
(E)

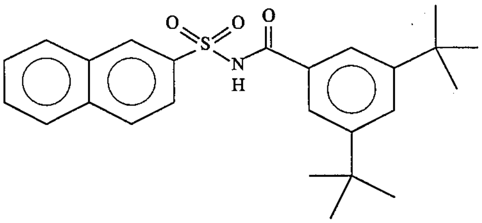
(F)

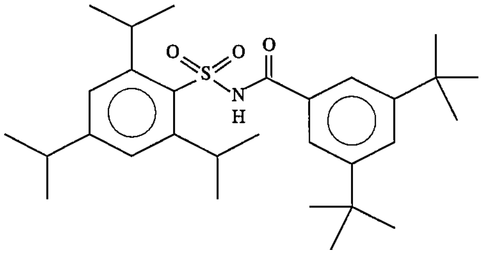
(G)

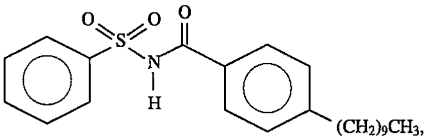
(H)

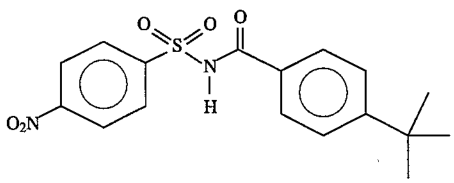
(I)

-continued
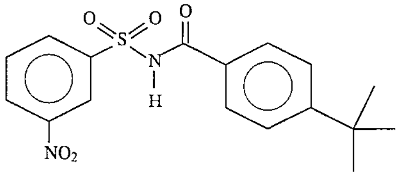
(J)
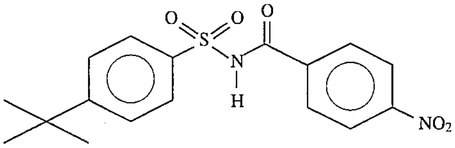
(K)
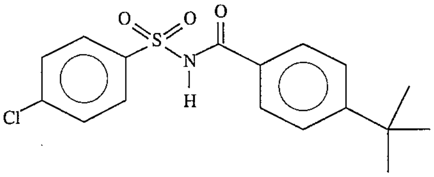
(L)
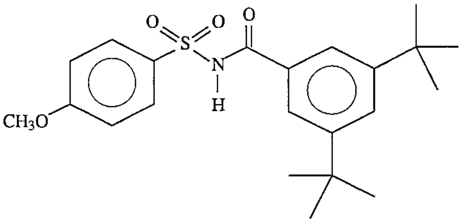
(M)
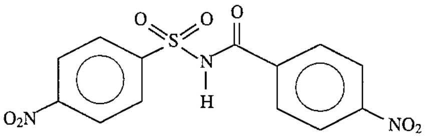
(N)
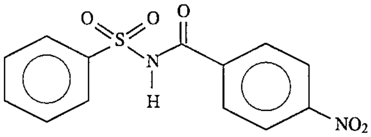
(O)
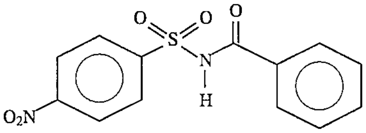
(P)
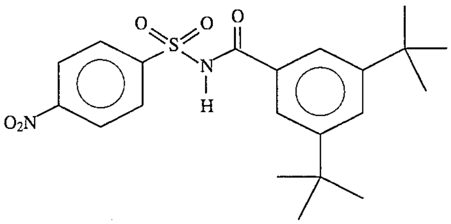
(Q)
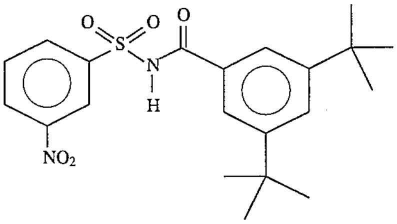
(R)
-continued
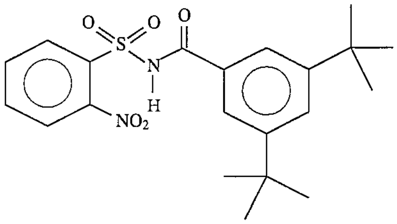
(S)
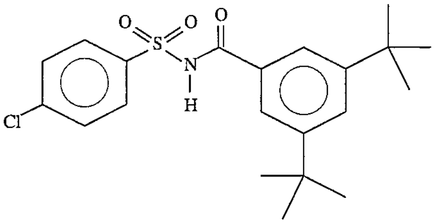
(T)
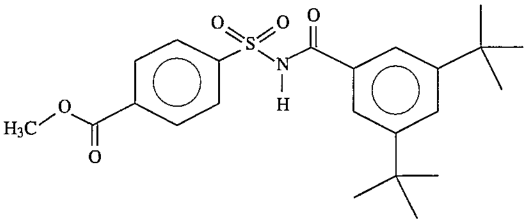
(U)
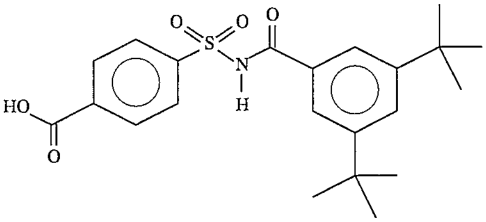
(V)
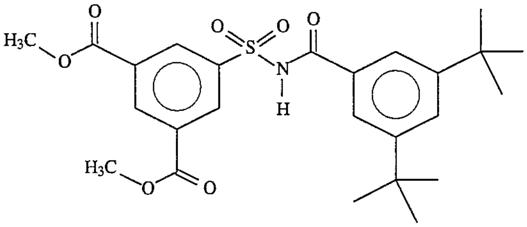
(W)
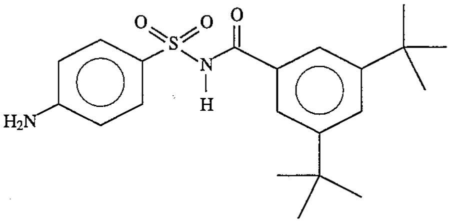
(X)
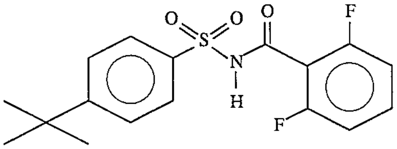
(Y)

-continued

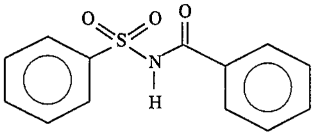

(Z)

EXAMPLES Z.A1, Z.A2

Sulfonamide charge control agent having the structural formula:

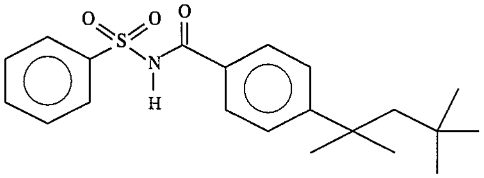

(Z.A)

was prepared as follows.

Preparation of 4-t-Octyltoluene 4-t-Octyltoluene was prepared as described in Journal of the American Chemical Society, Vol. 75, (1953) p. 6326.

Preparation of 4-t-Octylbenzoic acid

A mixture of 61.31 grams (0.30 mol) of 4-t-octyltoluene, 161.5 grams of pyridine, and 80.8 grams of 32% KOH was heated on a steam bath. To this mixture was added, in 10 gram portions every 30 minutes, 117.22 grams (0.74 mol) of $KMnO_4$. The reaction mixture was heated overnight and then 10 ml of ethanol was added. After 30 minutes, the mixture was filtered hot and the solid was washed with water. The combined filtrate and washes were heated for another 10 minutes on a steam bath and filtered again with water wash. The yellow filtrate comprised of two layers was acidified with concentrated HCl. On cooling, the upper layer crystallized. This solid was collected, washed with water and dried. The solid was washed with Ligroine (bp=35°–60° C.), dissolved in ether, washed with water, dried over $MgSO_4$ and concentrated. The residue was recrystallized from heptanes. Yield was 14.3 grams (20.34%). Melting point=153°–155° C. Elemental analysis found C=76.72, H=9.39. This compares to calculated values for $C_{15}H_{22}O_2$ of C=76.88, H=9.46. An NMR spectrum, in $CDCl_3$ was obtained in which agreed with the structure of the expected product.

Preparation of N-(4,t-octylbenzoyl)benzenesulfonamide

A solution of 25.28 grams (0.10 mol) of 4-t-octylbenzoyl chloride prepared from 4-t-octylbenzoic acid and oxaloyl chloride), 15.72 grams (0.10 mol) of benzenesulfonamide and 15.82 grams (0.20 mol) of pyridine was heated on a steam bath for 1.75 hours and cooled. The reaction mixture was dissolved in methylene chloride, washed twice with dilute HCl, then with water and finally with aqueous sodium chloride solution. The solution was dried over $MgSO_4$ and concentrated. The solid was treated with hot Ligroine (bp= 35°–60° C.), collected and dried. The solid was recrystallized from 1:1 heptane:toluene. Yield was 26.43 grams (70.8%). Melting point=146°–151.5° C. Elemental analysis found C=67.36, H=7.16, N=3.75, S=8.69. This compares to calculated values for $C_{21}H_{27}NO_3S$ of C=67.53, H=7.29, N=3.75, S=8.58. An NMR spectrum was obtained in which agreed with the structure of the expected product.

EXAMPLES Z.B1,Z.B2-Z.E1,Z.E2

The same procedures were substantially followed as described in Examples Z.A, except that starting materials in the aroylsulfonamide preparation were different. Toners and developers were prepared as in Examples A1, A2. Results are presented in Tables 2–3. The structural formulas of the sulfonamides utilized in these examples are:

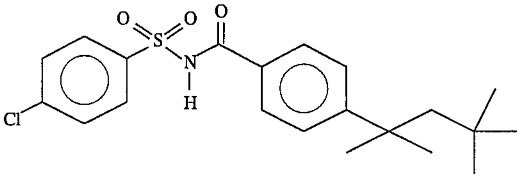

(Z.B)

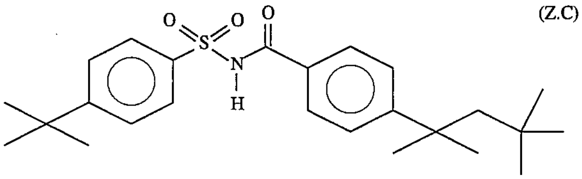

(Z.C)

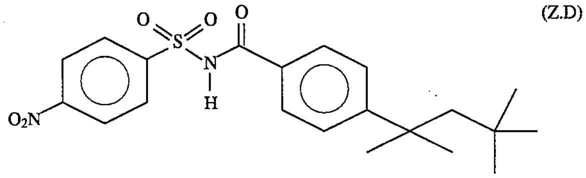

(Z.D)

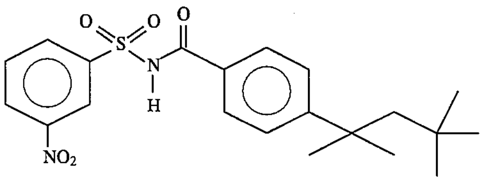

(Z.E)

TABLE 2

| | | Developer Using PMMA Coated Carrier | | | | | |
|---|---|---|---|---|---|---|---|
| Ex | CCA | m.p. (°C.) | Conc (pph) | P/S | 2 min | 10 min | T.O. (mg admix) |
| A1 | A | 232–234 | 1 | N | −15.3 | −39.5 | 1.2 |
| A1 | A | 232–234 | 2 | N | −17.5 | −40.7 | 0.3 |
| A1 | A | 232–234 | 4 | N | −29.0 | −38.2 | 0.2 |
| B1 | B | 221–222 | 1 | N | −13.4 | −27.5 | 4.3 |
| B1 | B | 221–222 | 2 | N | −17.2 | −23.6 | 1.6 |
| B1 | B | 221–222 | 4 | N | −24.6 | −22.8 | 1.2 |
| C1 | C | 195–197 | 1 | N | −10.6 | −35.8 | 6.4 |
| C1 | C | 195–197 | 2 | N | −13.2 | −32.5 | 2.5 |
| C1 | C | 195–197 | 4 | N | −17.3 | −32.1 | 1.1 |
| D1 | D | 192–194 | 1 | N | −12.9 | −43.9 | 4.3 |
| D1 | D | 192–194 | 2 | N | −14.7 | −39.9 | 4.4 |
| D1 | D | 192–194 | 4 | N | −19.1 | −42.2 | 1.2 |
| E1 | E | 232–233 | 1 | N | −14.9 | −44.7 | 3.3 |
| E1 | E | 232–233 | 2 | N | −23.2 | −41.9 | 1.4 |
| E1 | E | 232–233 | 4 | N | −23.3 | −41.8 | 1.2 |
| F1 | F | 236– | 1 | N | −18.4 | −38.1 | 6.2 |

TABLE 2-continued

Developer Using PMMA Coated Carrier

| Ex | CCA | m.p. (°C.) | Conc (pph) | P/S | 2 min | 10 min | T.O. (mg admix) |
|---|---|---|---|---|---|---|---|
| | | 237 | | | | | |
| F1 | F | 236–237 | 2 | N | −24.1 | −33.4 | 4.0 |
| F1 | F | 236–237 | 4 | N | −32.2 | −32.0 | 4.9 |
| G1 | G | 249 decomp | 1 | N | −20.5 | −28.9 | 5.7 |
| G1 | G | 249 decomp | 2 | N | −24.6 | −30.6 | 2.7 |
| G1 | G | 249 decomp | 4 | N | −28.2 | −26.0 | 5.2 |
| H1 | H | 98–99 | 1 | N | −13.3 | −47.7 | 2.8 |
| H1 | H | 98–99 | 2 | N | −14.4 | −41.5 | 1.1 |
| H1 | H | 98–99 | 4 | N | −14.8 | −42.1 | 1.8 |
| I1 | I | 210–212 | 1 | N | −18.0 | −34.0 | 3.1 |
| I1 | I | 210–212 | 2 | N | −19.7 | −26.9 | 1.9 |
| I1 | I | 210–212 | 4 | N | −26.7 | −22.3 | 1.9 |
| J1 | J | 231.5–233 | 1 | N | −20.5 | −28.5 | 6.9 |
| J1 | J | 231.5–233 | 2 | N | −27.5 | −25.6 | 2.4 |
| J1 | J | 231.5–233 | 4 | N | −35.3 | −23.2 | 6.3 |
| K1 | K | 241.5–243.5 | 1 | N | −22.2 | −26.4 | 3.4 |
| K1 | K | 241.5–243.5 | 2 | N | −27.4 | −21.3 | 2.5 |
| K1 | K | 241.5–243.5 | 4 | N | −32.1 | −19.0 | 1.0 |
| L1 | L | 214–215.5 | 1 | N | −16.5 | −39.3 | 5.2 |
| L1 | L | 214–215.5 | 2 | N | −18.8 | −37.1 | 3.7 |
| L1 | L | 214–215.5 | 4 | N | −36.7 | −31.3 | 3.0 |
| M1 | M | 185–187 | 1 | N | −13.6 | −32.6 | 4.1 |
| M1 | M | 185–187 | 2 | N | −18.4 | −38.4 | 2.2 |
| M1 | M | 185–187 | 4 | N | −21.1 | −36.0 | 2.8 |
| N1 | N | 223–225 | 1 | N | −14.2 | −12.9 | 38.9 |
| N1 | N | 223–225 | 2 | N | −17.2 | −8.1 | 58.8 |
| N1 | N | 223–225 | 4 | N | −13.4 | −3.3 | 131.2 |
| O1 | O | 213–214 | 1 | N | −17.6 | −20.0 | 6.0 |
| O1 | O | 213–214 | 2 | N | −18.8 | −15.5 | 10.2 |
| O1 | O | 213–214 | 4 | N | −20.2 | −13.1 | 27.5 |
| P1 | P | 199–201 | 1 | N | −20.8 | −29.7 | 4.9 |
| P1 | P | 199–201 | 2 | N | −18.7 | −20.3 | 5.0 |
| P1 | P | 199–201 | 4 | N | −20.8 | −19.9 | 5.2 |
| Q1 | Q | 267–268 | 1 | N | −26.8 | −26.5 | 1.5 |
| Q1 | Q | 267–268 | 2 | N | −39.5 | −22.6 | 1.5 |
| Q1 | Q | 267–268 | 4 | N | −47.6 | −23.5 | 1.4 |
| R1 | R | 236–237 | 1 | N | −21.5 | −24.6 | 0.9 |
| R1 | R | 236–237 | 2 | N | −38.0 | −30.9 | 1.1 |
| R1 | R | 236–237 | 4 | N | −51.9 | −30.2 | 0.6 |
| S1 | S | 195–197 | 1 | N | −15.7 | −33.5 | 1.7 |
| S1 | S | 195–197 | 2 | N | −18.9 | −29.6 | 0.7 |
| S1 | S | 195–197 | 4 | N | −21.8 | −27.7 | 1.0 |
| T1 | T | 249–251 | 1 | N | −22.5 | −23.6 | 0.7 |
| T1 | T | 249–251 | 2 | N | −32.9 | −24.9 | 0.8 |
| T1 | T | 249–251 | 4 | N | −40.0 | −25.3 | 0.8 |
| U1 | U | 225–227.5 | 1 | N | −14.8 | −35.7 | 2.0 |
| U1 | U | 225–227.5 | 2 | N | −28.3 | −31.7 | 0.7 |
| U1 | U | 225–227.5 | 4 | N | −37.0 | −31.8 | 0.9 |
| V1 | V | 289 | 1 | Y | −16.8 | −20.5 | 4.3 |
| V1 | V | 289 | 2 | Y | −20.1 | −21.5 | 2.0 |
| V1 | V | 289 | 4 | Y | −24.8 | −24.6 | 1.2 |
| W1 | W | 193–198 | 1 | N | −16.5 | −35.7 | 1.7 |
| W1 | W | 193–198 | 2 | N | −18.2 | −32.3 | 1.6 |
| W1 | W | 193–198 | 4 | N | −29.6 | −29.8 | 1.2 |
| X1 | X | 251 | 1 | Y | −19.1 | −33.0 | 4.2 |
| X1 | X | 251 | 2 | Y | −20.5 | −27.3 | 1.0 |
| X1 | X | 251 | 4 | Y | −22.9 | −23.6 | 2.0 |
| Y1 | Y | 113–115 | 1 | N | −11.3 | −31.7 | 6.5 |
| Y1 | Y | 113–115 | 2 | N | −14.1 | −30.3 | 4.3 |
| Y1 | Y | 113–115 | 4 | N | −15.7 | −32.3 | 5.7 |
| Z1 | Z | 145.5–146.5 | 1 | N | −16.2 | −29.5 | 4.9 |
| Z1 | Z | 145.5–146.5 | 2 | N | −17.7 | −31.2 | 3.9 |
| Z1 | Z | 145.5–146.5 | 4 | N | −18.8 | −23.9 | 2.5 |
| Z.A1 | Z.A | 146–151.5 | 1 | N | −14.8 | −34.9 | 1.8 |
| Z.A1 | Z.A | 146–151.5 | 2 | N | −14.6 | −31.0 | 1.4 |
| Z.A1 | Z.A | 146–151.5 | 4 | N | −16.0 | −27.7 | 1.4 |
| Z.B1 | Z.B | 114.5–118 | 1 | N | −16.0 | −33.1 | 2.8 |
| Z.B1 | Z.B | 114.5–118 | 2 | N | −18.7 | −29.4 | 2.4 |
| Z.B1 | Z.B | 114.5–118 | 4 | N | −19.9 | −30.6 | 2.5 |
| Z.C1 | Z.C | 172–173.5 | 1 | N | −14.4 | −37.9 | 1.1 |
| Z.C1 | Z.C | 172–173.5 | 2 | N | −15.5 | −28.7 | 1.8 |
| Z.C1 | Z.C | 172–173.5 | 4 | N | −16.8 | −28.7 | 1.3 |
| Z.D1 | Z.D | 137.5–141 | 1 | N | −18.1 | −32.9 | 3.6 |
| Z.D1 | Z.D | 137.5–141 | 2 | N | −18.3 | −26.0 | 1.1 |
| Z.D1 | Z.D | 137.5–141 | 4 | N | −22.2 | −25.2 | 2.3 |
| Z.E1 | Z.E | 133–135 | 1 | N | −15.5 | −29.7 | 2.5 |

TABLE 2-continued

| Developer Using PMMA Coated Carrier | | | | | | | |
|---|---|---|---|---|---|---|---|
| Ex | CCA | m.p. (°C.) | Conc (pph) | P/S | 2 min | 10 min | T.O. (mg admix) |
| Z.E 1 | Z.E | 133–135 | 2 | N | −20.9 | −24.7 | 3.0 |
| Z.E 1 | Z.E | 133–135 | 4 | N | −20.6 | −22.1 | 4.0 |

TABLE 3

| Developer Using Modified Kynar Carrier | | | | | | | |
|---|---|---|---|---|---|---|---|
| Ex | CCA | m.p. (°C.) | Conc (pph) | P/S | 2 min | 10 min | T.O. (mg admix) |
| A2 | A | 232–234 | 1 | N | −8.8 | −49.7 | 0.2 |
| A2 | A | 232–234 | 2 | N | −20.3 | −55.6 | 0.2 |
| A2 | A | 232–234 | 4 | N | −26.4 | −33.5 | 0 |
| B2 | B | 221–222 | 1 | N | −4.3 | −36.4 | 0.2 |
| B2 | B | 221–222 | 2 | N | −9.0 | −36.0 | 0.1 |
| B2 | B | 221–222 | 4 | N | −21.6 | −38.9 | 0.4 |
| C2 | C | 195–197 | 1 | N | −6.2 | −53.0 | 0.3 |
| C2 | C | 195–197 | 2 | N | −8.3 | −53.5 | 0.3 |
| C2 | C | 195–197 | 4 | N | −10.6 | −50.7 | 0.2 |
| D2 | D | 192–194 | 1 | N | −4.5 | −64.0 | 0.3 |
| D2 | D | 192–194 | 2 | N | −8.5 | −58.2 | 0.5 |
| D2 | D | 192–194 | 4 | N | −18.6 | −65.3 | 0.3 |
| E2 | E | 232–233 | 1 | N | −20.0 | −66.4 | 0.3 |
| E2 | E | 232–233 | 2 | N | −23.3 | −58.6 | 0.3 |
| E2 | E | 232–233 | 4 | N | −30.5 | −56.8 | 0.3 |
| F2 | F | 236–237 | 1 | N | −12.8 | −65.3 | 0.3 |
| F2 | F | 236–237 | 2 | N | −17.9 | −46.3 | 0 |
| F2 | F | 236–237 | 4 | N | −26.5 | −47.9 | 0.2 |
| G2 | G | 249 decomp | 1 | N | −16.4 | −45.3 | 0.4 |
| G2 | G | 249 decomp | 2 | N | −24.2 | −49.6 | 0.3 |
| G2 | G | 249 decomp | 4 | N | −35.8 | −43.4 | 0.3 |
| H2 | H | 98–99 | 1 | N | −6.6 | −66.1 | 0.4 |
| H2 | H | 98–99 | 2 | N | −6.1 | −54.7 | 0.2 |
| H2 | H | 98–99 | 4 | N | −7.4 | −56.4 | 0.2 |
| I2 | I | 210–212 | 1 | N | — | — | — |
| I2 | I | 210–212 | 2 | N | — | — | — |
| I2 | I | 210–212 | 4 | N | −28.3 | −16.6 | 2.3 |
| J2 | J | 231.5–233 | 1 | N | −6.7 | −48.5 | 0.4 |
| J2 | J | 231.5–233 | 2 | N | −22.8 | −30.7 | 1.5 |
| J2 | J | 231.5–233 | 4 | N | −42.2 | −27.8 | 6.1 |
| K2 | K | 241.5– | 1 | N | −11.1 | −52.8 | 0.7 |

TABLE 3-continued

| Developer Using Modified Kynar Carrier | | | | | | | |
|---|---|---|---|---|---|---|---|
| Ex | CCA | m.p. (°C.) | Conc (pph) | P/S | 2 min | 10 min | T.O. (mg admix) |
| | | 243.5 | | | | | |
| K2 | K | 241.5–243.5 | 2 | N | −23.4 | −22.2 | 1.7 |
| K2 | K | 241.5–243.5 | 4 | N | −30.0 | −14.9 | 4.7 |
| L2 | L | 214–215.5 | 1 | N | −3.9 | −62.0 | 0.8 |
| L2 | L | 214–215.5 | 2 | N | −4.3 | −46.0 | 0.8 |
| L2 | L | 214–215.5 | 4 | N | −19.4 | −57.0 | 0.7 |
| M2 | M | 185–187 | 1 | N | −5.8 | −56.9 | 0.8 |
| M2 | M | 185–187 | 2 | N | −9.6 | −43.9 | 0.6 |
| M2 | M | 185–187 | 4 | N | −15.4 | −50.6 | 0.3 |
| N2 | N | 223–235 | 1 | N | −6.0 | −29.1 | 3.3 |
| N2 | N | 233–235 | 2 | N | −14.2 | −12.7 | 13.6 |
| N2 | N | 233–235 | 4 | N | −11.7 | −2.6 | 176.7 |
| O2 | O | 213–214 | 1 | N | −13.0 | −39.1 | 0.5 |
| O2 | O | 213–214 | 2 | N | −13.9 | −10.0 | 5.2 |
| O2 | O | 213–214 | 4 | N | −14.6 | −1.4 | 129.3 |
| PP2 | P | 199–201 | 1 | N | −8.8 | −50.1 | 0.9 |
| P2 | P | 199–201 | 2 | N | −11.1 | −18.3 | 3.7 |
| P2 | P | 199–201 | 4 | N | −16.2 | −1.4 | 53.9 |
| Q2 | Q | 267–268 | 1 | N | −21.2 | −40.2 | 0.3 |
| Q2 | Q | 267–268 | 2 | N | −28.1 | −32.4 | 0.8 |
| Q2 | Q | 267–268 | 4 | N | −30.5 | −32.7 | 1.2 |
| R2 | R | 236–237 | 1 | N | −12.6 | −44.9 | 0.1 |
| R2 | R | 236–237 | 2 | N | −35.1 | −51.1 | 0.4 |
| R2 | R | 236–237 | 4 | N | −58.2 | −59.7 | 0.3 |
| S2 | S | 195–197 | 1 | N | −13.4 | −57.4 | 0.2 |
| S2 | S | 195–197 | 2 | N | −11.4 | −48.4 | 0.2 |
| S2 | S | 195–197 | 4 | N | −15.7 | −47.6 | 0.3 |
| T2 | T | 249–251 | 1 | N | −21.1 | −41.3 | 0.3 |
| T2 | T | 249–251 | 2 | N | −37.4 | −50.2 | 0.1 |
| T2 | T | 249–251 | 4 | N | −45.8 | −53.0 | 0.2 |
| U2 | U | 225–227.5 | 1 | N | −5.3 | −60.2 | 1.1 |
| U2 | U | 225–227.5 | 2 | N | −21.9 | −45.5 | 0.6 |
| U2 | U | 225–227.5 | 4 | N | −45.7 | −57.7 | 0.3 |
| V2 | V | 289 | 1 | N | −7.5 | −17.7 | 1.8 |
| V2 | V | 289 | 2 | N | −9.6 | −9.6 | 2.2 |
| V2 | V | 289 | 4 | N | −14.1 | −14.5 | 2.0 |
| W2 | W | 193–198 | 1 | N | −7.3 | −59.7 | 0.4 |
| W2 | W | 193–198 | 2 | N | −8.7 | −51.3 | 0.4 |
| W2 | W | 193– | 4 | N | −30.8 | −45.6 | 0.3 |

TABLE 3-continued

| Developer Using Modified Kynar Carrier | | | | | | | |
|---|---|---|---|---|---|---|---|
| Ex | CCA | m.p. (°C.) | Conc (pph) | P/S | 2 min | 10 min | T.O. (mg admix) |
| | | 198 | | | | | |
| X2 | X | 251 | 1 | N | −21.1 | −44.1 | 0.5 |
| X2 | X | 251 | 2 | N | −20.2 | −35.4 | 1.0 |
| X2 | X | 251 | 4 | N | −25.2 | −34.1 | 1.3 |
| Y2 | Y | 113–115 | 1 | Y | −12.1 | −51.7 | 0.5 |
| Y2 | Y | 113–115 | 2 | Y | −9.4 | −43.3 | 0.2 |
| Y2 | Y | 113–115 | 4 | Y | −9.4 | −38.5 | 0.5 |
| Z2 | Z | 145.5–146.5 | 1 | N | −5.1 | −43.9 | 1.5 |
| Z2 | Z | 145.5–146.5 | 2 | N | −2.6 | −36.6 | 1.7 |
| Z2 | Z | 145.5–146.5 | 4 | N | −2.5 | −24.7 | 1.5 |
| Z.A 1 | Z.A | 146–151.5 | 1 | N | −10.2 | −59.2 | 0.2 |
| Z.A 1 | Z.A | 146–151.5 | 2 | N | −8.1 | −50.9 | 0.0 |
| Z.A. 1 | Z.A | 146–151.5 | 4 | N | −8.4 | −40.2 | 0.0 |
| Z.B 1 | Z.B | 114.5–118 | 1 | N | −14.9 | −59.0 | 0.2 |
| Z.B 1 | Z.B | 114.5–118 | 2 | N | −12.9 | −48.5 | 0.4 |
| Z.B 1 | Z.B | 114.5–118 | 4 | N | −15.7 | −39.5 | 0.1 |
| Z.C 1 | Z.C | 172–173.5 | 1 | N | −8.7 | −60.5 | 0.0 |
| Z.C 1 | Z.C | 172–173.5 | 2 | N | −9.7 | −53.2 | 0.0 |
| Z.C 1 | Z.C | 172–173.5 | 4 | N | −11.1 | −47.6 | 0.2 |
| Z.D 1 | Z.D | 137.5–141 | 1 | N | −13.9 | −63.7 | 0.2 |
| Z.D 1 | Z.D | 137.5–141 | 2 | N | −15.4 | −49.8 | 0.0 |
| Z.D 1 | Z.D | 137.5–141 | 4 | N | −18.3 | −37.5 | 0.4 |
| Z.E 1 | Z.E | 133–135 | 1 | N | −14.5 | −59.2 | 0.0 |
| Z.E 1 | Z.E | 133–135 | 2 | N | −13.7 | −49.7 | 0.3 |
| Z.E 1 | Z.E | 133–135 | 4 | N | −16.3 | −37.2 | 0.4 |

EXAMPLES AA1, AA2

Sulfonamide charge control agent having the structural formula:

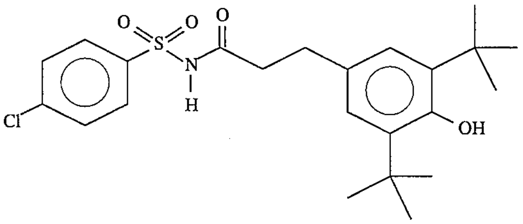

(AA)

was prepared as follows. 3-(3,5-di-t-butyl-4-hydroxyphenyl)propionic acid was prepared by the method described in U.S. Pat. No. 4,205,176 from 2,6-di-t-butyl phenol and acrylonitrile in accord with the reaction scheme:

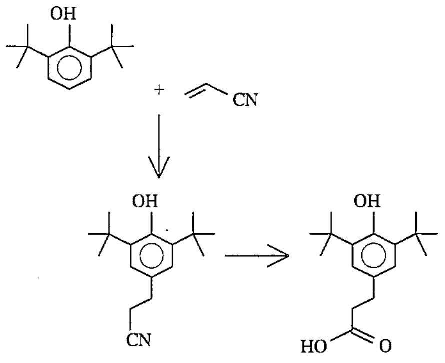

3-(3,5-di-t-butyl-4-hydroxyphenyl)propionyl chloride was prepared from 3-(3,5-di-t-butyl-4-hydroxyphenyl)propionic acid and oxalyl chloride in accord with the reaction scheme:

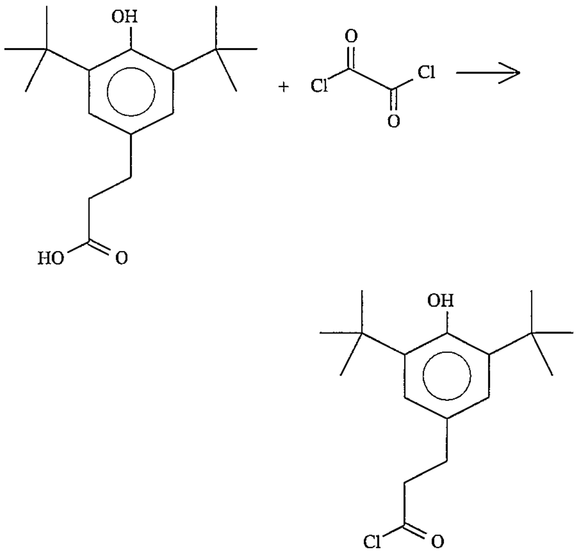

A mixture of 4-chlorobenzedsulfonamide (9.58 g, 0.05 mol), 3-(3,5-di-t-butyl-4-hydroxyphenyl)propionyl chloride (14.84 g, 0.05 mol), and toluene (100 ml) was prepared and heated at reflux. A complete solution was obtained and acidic vapors were emitted. Refluxing was continued for about 22.5 hours. After cooling, the solution was concentrated on a rotary evaporator to obtain an oily residue. The residue was stirred with ligroine (bp=35°–60° C. ), from which a crystalline precipitate was obtained. The crystalline material was collected and recrystallized from 100 ml of 1 to 1 heptane:toluene. The resulting solid was collected with 1 to 1 heptane:toluene rinse, washed with ligroine (bp=35°–60° C.) and dried. Yield was 17.9 grams (79.2%). Melting point was 166.5°–171° C. Elemental analysis found C=60.63, H=6.59, N=3.00, Cl=8.19, S=7.08. This compares to calculated values for $C_{23}H_{30}ClNO_4S$ of C=61.12, H=6.69, N=3.10, Cl=7.84, S=7.09. An NMR spectrum was obtained in deuterated chloroform which agreed with the structure of the expected product.

The same procedures were substantially followed in the preparation of toners and developers and in evaluating materials as described in Examples A, except that only colorless toners were produced. Results are presented in Tables 4–5.

EXAMPLES AB1, AB2

Sulfonamide charge control agent having the structural formula:

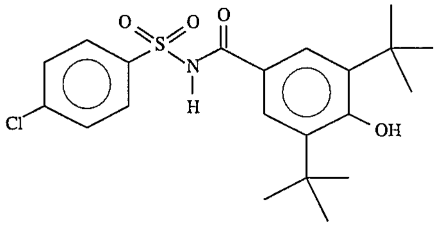

(AB)

was prepared in accord with the reaction scheme:

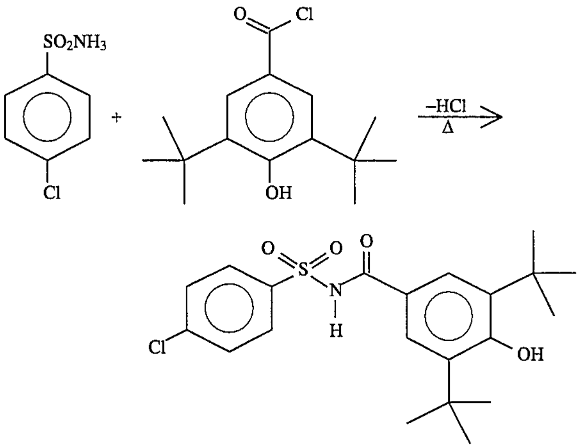

as follows. A mixture of 4-chlorobenzedsulfonamide (9.58 g, 0.050 mol), 3,5-di-t-butyl-4-hydroxy-benzoyl chloride (13.44 g, 0.050 mol), and toluene (100 ml) was prepared and heated at reflux. A complete solution was obtained and acidic vapors were emitted. Refluxing was continued for about 18.5 hours. During this time, solid precipitated. At the end of this time, the evolution of acidic vapors had stopped. After cooling, a white solid was collected, washed with ligroine (bp=35°–60° C.) and dried. This material was recrystallized from 550 ml of acetonitrile, collected and dried. Yield was 16.8 grams (79.25%). Melting point was 260°–261.5° C. Elemental analysis found C=59.05, H=6.08, N=3.49, Cl=8.98, S=7.40. This compares to calculated values for $C_{21}H_{26}ClNO_4S$ of C=59.49H=6.18, N=3.30, Cl=8.36, S=7.56. NMR spectrum, in deuterated chloroform, was obtained which agreed with the structure of the expected product.

The same procedures were substantially followed in the preparation of toners and developers and in evaluating materials as described in Examples A, except that only colorless toners were produced. Results are presented in Tables 4–5.

EXAMPLES AC1, AC2-AO.B1,AO.B2

The same procedures were substantially followed as described in Examples AB, except that starting materials in the aroylsulfonamide preparation were different, Examples AE were prepared in xylenes as solvent, and Examples AN were prepared with pyridine and 4-dimethylaminopyridine in tetrahydrofuran. Results are presented in Tables 4–5. Sulfonamides utilized in these examples are indicated by the designations on the following structural formulas:

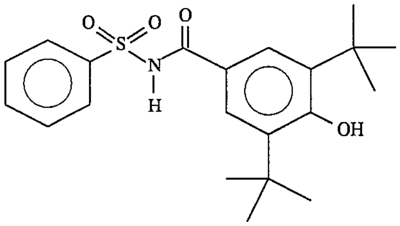

(AC)

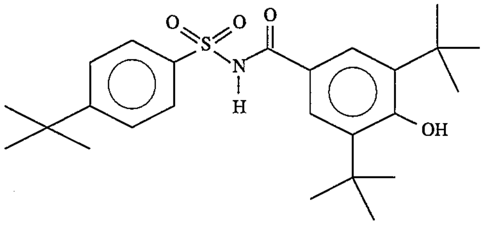

(AD)

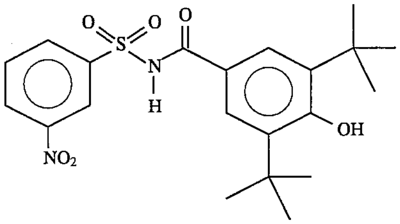

(AE)

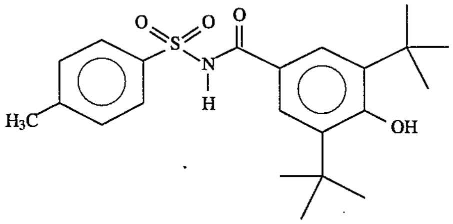

(AF)

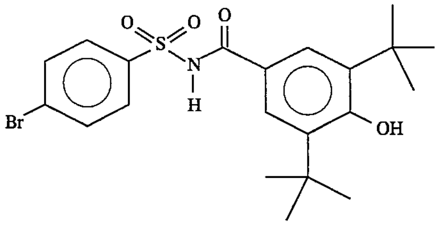

(AG)

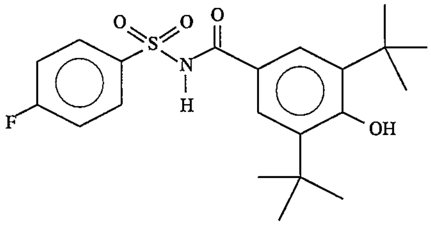

(AH)

-continued (AI)

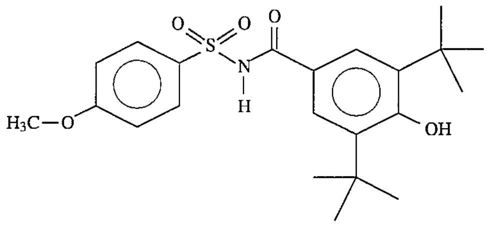

(AJ)

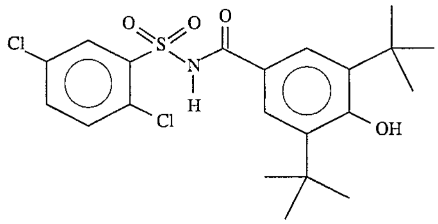

(AK)

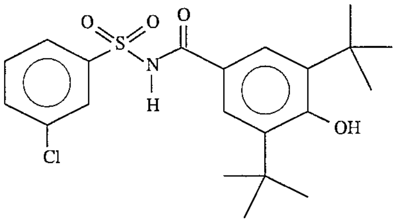

(AL)

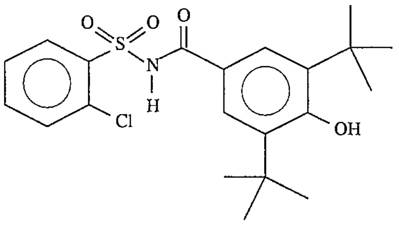

(AM)

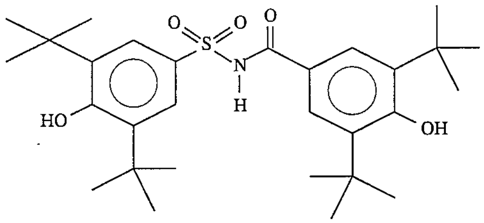

(AN)

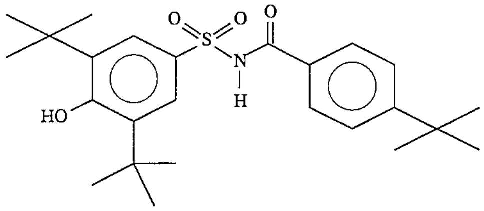

(AO)

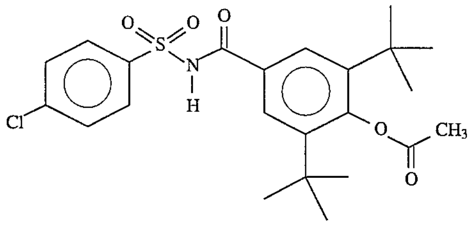

-continued (AO.A)

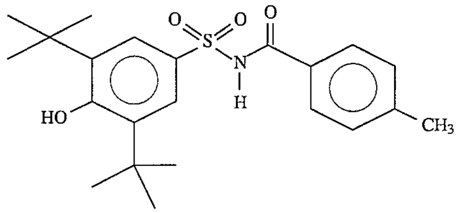

(AO.B)

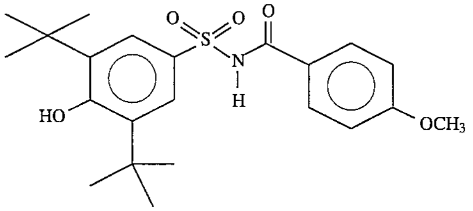

EXAMPLES AO.C1,AO.C2

Sulfonamide charge control agent having the structural formula:

(AO.C)

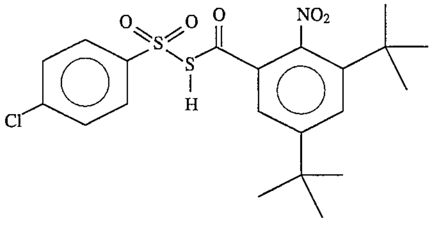

was prepared in accord with the reaction scheme:

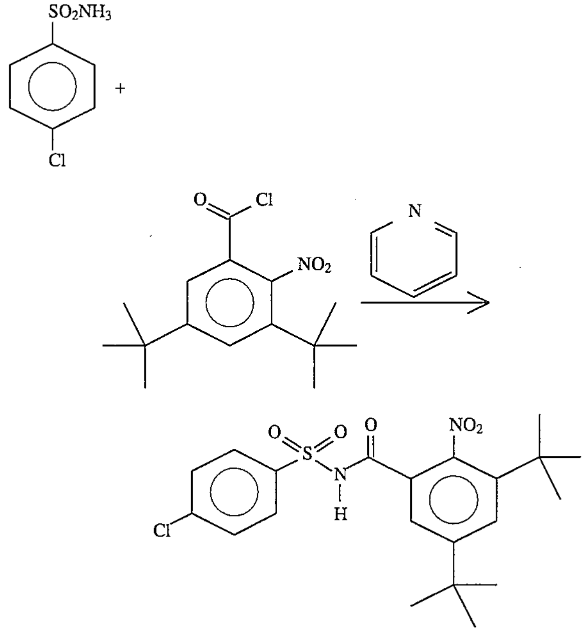

as follows.

3,5-Di-t-butyl-2-nitrobenzoyl chloride was prepared by nitration of 3,5-di-t-butylbenzoic acid 46.86 grams (0.20 mol) with 90% nitric acid (150 ml, d=1.5) to give 3,5-di-t-butyl-2-nitrobenzoic acid (54.6 grams) followedby treatment with thionyl chloride (250 ml) with dimethylformamide (1 ml).

A mixture of 3,5-di-t-butyl-2-nitro-benzoyl chloride (29.78 g, 0.10 mol), 4-chlorobenzedsulfonamide (19.16 g, 0.10 mol), and pyridine (15.82 grams, 0.20 mol) was prepared and heated on a steam bath, with stirring. After five minutes, 50 ml of tetrahydrofuran was added. Another 50 ml of tetrahydrofuran was added after 10 minutes. After about 1.5 hours, the reaction mixture was cooled and poured into dilute HCl. An oily precipitate crystallized, was collected, and was washed twice with water. The product was recrystallized from isopropanol, collected and dried. Yield was 31.55 grams (69.7%). Melting point was 243°–248° C . Elemental analysis found C=55.39, H=5.62, N=6.25, Cl=7.90, S=7.52. This compares to calculated values for $C_{21}H_{25}ClN_2O_5S$ of C=55.69, H=5.56, N=6.18, Cl=7.83, S=7.08. An NMR spectrum was obtained which agreed with the structure of the expected product.

The same procedures were substantially followed in the preparation of toners and developers and in evaluating materials as described in Examples A, except that only colorless toners were produced. Results are presented in Tables 4–5.

TABLE 4

| Developer Using PMMA Coated Carrier | | | | | | | |
|---|---|---|---|---|---|---|---|
| Ex | CCA | m.p. (°C.) | Conc (pph) | P/S | 2 min | 10 min | T.O. (mg admix) |
| AA1 | AA | 166.5–171 | 1 | N | −12.6 | −48.9 | 2.5 |
| AA1 | AA | 166.5–171 | 2 | N | −13.4 | −44.8 | 1.7 |
| AA1 | AA | 166.5–171 | 4 | N | −15.4 | −34.2 | 3.0 |
| AB1 | AB | 260–261.5 | 1 | N | −28.0 | −32.3 | 1.1 |
| AB1 | AB | 260–261.5 | 2 | N | −30.5 | −25.5 | 1.8 |
| AB1 | AB | 260–261.5 | 4 | N | −36.9 | −21.7 | 1.6 |
| AC1 | AC | 205–208 | 1 | N | −17.1 | −45.0 | 3.3 |
| AC1 | AC | 205–208 | 2 | N | −21.1 | −41.0 | 2.9 |
| AC1 | AC | 205–208 | 4 | N | −27.1 | −32.0 | 1.8 |
| AD1 | AD | 256–258 | 1 | N | −18.5 | −40.6 | 0.4 |
| AD1 | AD | 256–258 | 2 | N | −23.4 | −30.4 | 0.5 |
| AD1 | AD | 256–258 | 4 | N | −30.4 | −26.6 | 0.7 |
| AE1 | AE | 206–212 | 1 | N | −18.7 | −43.9 | 0.7 |
| AE1 | AE | 206–212 | 2 | N | −25.9 | −36.7 | 0.9 |
| AE1 | AE | 206–212 | 4 | N | −36.4 | −26.2 | 1.2 |
| AF1 | AF | 222–225.5 | 1 | N | −20.3 | −43.8 | 1.1 |
| AF1 | AF | 222–225.5 | 2 | N | −21.8 | −34.6 | 2.7 |
| AF1 | AF | 222–225.5 | 4 | N | −32.0 | −24.3 | 1.6 |
| AG1 | AG | 267–268.5 | 1 | N | −28.1 | −36.8 | 0.8 |
| AG1 | AG | 267–268.5 | 2 | N | −34.7 | −33.7 | 1.2 |
| AG1 | AG | 267–268.5 | 4 | N | −36.6 | −23.8 | 1.2 |
| AH1 | AH | 224–227 | 1 | N | −21.3 | −40.7 | 1.4 |
| AH1 | AH | 224–227 | 2 | N | −30.8 | −33.5 | 1.3 |

TABLE 4-continued

| Developer Using PMMA Coated Carrier | | | | | | | |
|---|---|---|---|---|---|---|---|
| Ex | CCA | m.p. (°C.) | Conc (pph) | P/S | 2 min | 10 min | T.O. (mg admix) |
| AH1 | AH | 224–227 | 4 | N | −34.3 | −23.9 | 1.6 |
| AI1 | AI | 216.5–218.5 | 1 | N | −18.5 | −45.8 | 0.9 |
| AI1 | AI | 216.5–218.5 | 2 | N | −24.7 | −34.8 | 1.7 |
| AI1 | AI | 216.5–218.5 | 4 | N | −29.3 | −27.5 | 2.3 |
| AJ1 | AJ | 242–245 | 1 | N | −16.3 | −41.4 | 0.9 |
| AJ1 | AJ | 242–245 | 2 | N | −22.9 | −34.1 | 1.1 |
| AJ1 | AJ | 242–245 | 4 | N | −30.2 | −28.1 | 2.0 |
| AK1 | AK | 192.5–195 | 1 | N | −19.9 | −44.9 | 1.6 |
| AK1 | AK | 192.5–195 | 2 | N | −26.2 | −46.8 | 1.0 |
| AK1 | AK | 192.5–195 | 4 | N | −29.4 | −34.7 | 1.1 |
| AL1 | AL | 248.5–249.5 | 1 | N | −23.2 | −44.0 | 0.9 |
| AL1 | AL | 248.5–249.5 | 2 | N | −25.6 | −34.9 | 0.8 |
| AL1 | AL | 248.5–249.5 | 4 | N | −27.6 | −27.7 | 1.1 |
| AM1 | AM | 245–248 | 1 | N | −18.2 | −34.5 | 0.9 |
| AM1 | AM | 245–248 | 2 | N | −19.9 | −29.5 | 1.5 |
| AM1 | AM | 245–248 | 4 | N | −22.0 | −22.8 | 1.6 |
| AN1 | AN | 246–248.5 | 1 | N | −14.6 | −36.4 | 2.8 |
| AN1 | AN | 246–248.5 | 2 | N | −22.7 | −30.7 | 2.0 |
| AN1 | AN | 246–248.5 | 4 | N | −22.0 | −20.3 | 0.8 |
| AO1 | AO | 186–189 | 1 | N | −13.2 | −33.4 | 2.7 |
| AO1 | AO | 186–189 | 2 | N | −19.8 | −34.8 | 0.9 |
| AO1 | AO | 186–189 | 4 | N | −25.1 | −30.7 | 0.5 |
| AO.A1 | AO.A | 235.5–237 | 1 | N | −19.2 | −38.3 | 0.7 |
| AO.A1 | AO.A | 235.5–237 | 2 | N | −19.7 | −28.5 | 0.9 |
| AO.A1 | AO.A | 235.5–237 | 4 | N | −25.7 | −29.0 | 1.7 |
| AO.B1 | AO.B | 220–211.5 | 1 | N | −17.7 | −44.7 | 1.0 |
| AO.B1 | AO.B | 220–221.5 | 2 | N | −20.7 | −32.8 | 1.5 |
| AO.B1 | AO.B | 220–221.5 | 4 | N | −24.9 | −28.3 | 1.5 |
| AO.C1 | AO.C | 246–249 | 1 | N | −18.9 | −28.4 | 1.4 |
| AO.C1 | AO.C | 246–249 | 2 | N | −25.8 | −26.9 | 0.8 |
| AO.C1 | AO.C | 246–249 | 4 | N | −28.3 | −23.1 | 0.8 |

TABLE 5

| | | Developer Using Modified Kynar Carrier | | | | | |
|---|---|---|---|---|---|---|---|
| Ex | CCA | m.p. (°C.) | Conc (pph) | P/S | 2 min | 10 min | T.O. (mg admix) |
| AA2 | AA | 166.5–171 | 1 | N | −32.8 | −71.8 | 0.2 |
| AA2 | AA | 166.5–171 | 2 | N | −39.8 | −69.7 | 0.2 |
| AA2 | AA | 166.5–171 | 4 | N | −36.8 | −54.2 | 0 |
| AB2 | AB | 260–261.5 | 1 | N | −29.4 | −43.9 | 0.7 |
| AB2 | AB | 260–261.5 | 2 | N | −36.5 | −32.4 | 1.1 |
| AB2 | AB | 260–261.5 | 4 | N | −35.3 | −26.6 | 1.8 |
| AC2 | AC | 205–208 | 1 | N | −29.2 | −65.5 | 0.0 |
| AC2 | AC | 205–208 | 2 | N | −37.1 | −53.8 | 0.2 |
| AC2 | AC | 205–208 | 4 | N | −34.4 | −34.5 | 0.9 |
| AD2 | AD | 256–258 | 1 | N | −25.8 | −52.2 | 0 |
| AD2 | AD | 256–258 | 2 | N | −29.3 | −40.8 | 0.3 |
| AD2 | AD | 256–258 | 4 | N | −36.1 | −48.4 | 0.3 |
| AE2 | AE | 206–212 | 1 | N | −20.7 | −63.2 | 0.3 |
| AE2 | AE | 206–212 | 2 | N | −31.2 | −56.8 | 0.2 |
| AE2 | AE | 206–212 | 4 | N | −41.3 | −32.1 | 0.7 |
| AF2 | AF | 222–225.5 | 1 | N | −25.2 | −62.5 | 0.1 |
| AF2 | AF | 222–225.5 | 2 | N | −30.1 | −43.6 | 0.2 |
| AF2 | AF | 222–225.5 | 4 | Y | −33.9 | −28.7 | 2.8 |
| AG2 | AG | 267–268.5 | 1 | N | −29.5 | −53.1 | 0.0 |
| AG2 | AG | 267–268.5 | 2 | N | −32.6 | −33.6 | 0.8 |
| AG2 | AG | 267–268.5 | 4 | N | −33.6 | −22.8 | 5.7 |
| AH2 | AH | 224–227 | 1 | N | −25.3 | −59.7 | 0.1 |
| AH2 | AH | 224–227 | 2 | N | −33.4 | −40.0 | 0.6 |
| AH2 | AH | 224–227 | 4 | N | −28.6 | −23.8 | 2.0 |
| AI2 | AI | 216.5–218.5 | 1 | N | −20.0 | −59.9 | 0.3 |
| AI2 | AI | 216.5–218.5 | 2 | N | −30.6 | −42.5 | 0.6 |
| AI2 | AI | 216.5–218.5 | 4 | N | −34.6 | −27.8 | 3.0 |
| AJ2 | AJ | 242–245 | 1 | N | −13.9 | −59.2 | 0.1 |
| AJ2 | AJ | 242–245 | 2 | N | −21.8 | −46.6 | 0.4 |
| AJ2 | AJ | 242–245 | 4 | N | 28.1 | −33.3 | 1.0 |
| AK2 | AK | 192.5–195 | 1 | N | −33.3 | −71.1 | 0.0 |
| AK2 | AK | 192.5–195 | 2 | N | −39.2 | −60.2 | 0.1 |
| AK2 | AK | 192.5–195 | 4 | N | −38.0 | −37.9 | 0.5 |
| AL2 | AL | 248.5–249.5 | 1 | N | −32.9 | −64.6 | 0.2 |
| AL2 | AL | 248.5–249.5 | 2 | N | −36.3 | −43.8 | 0.4 |
| AL2 | AL | 248.5–249.5 | 4 | N | −35.5 | −27.9 | 1.1 |
| AM2 | AM | 245– | 1 | N | −21.4 | −49.0 | 0.3 |

TABLE 5-continued

| | | Developer Using Modified Kynar Carrier | | | | | |
|---|---|---|---|---|---|---|---|
| Ex | CCA | m.p. (°C.) | Conc (pph) | P/S | 2 min | 10 min | T.O. (mg admix) |
| | | 248 | | | | | |
| AM2 | AM | 245–248 | 2 | N | −22.8 | −33.1 | 0.3 |
| AM2 | AM | 245–248 | 4 | N | −28.0 | −28.0 | 0.6 |
| AN2 | AN | 246–248.5 | 1 | N | −17.4 | −50.3 | 0.2 |
| AN2 | AN | 246–248.5 | 2 | N | −24.0 | −44.6 | 0.4 |
| AN2 | AN | 246–248.5 | 4 | N | −22.2 | −28.8 | 0.9 |
| AO2 | AO | 186–189 | 1 | N | −6.5 | −51.3 | 0.2 |
| AO2 | AO | 186–189 | 2 | N | −6.6 | −52.8 | 0.1 |
| AO2 | AO | 186–189 | 4 | N | −13.0 | −41.1 | 0.4 |
| AO.A2 | AO.A | 235.5–237 | 1 | N | −23.3 | −51.0 | 0.3 |
| AO.A2 | AO.A | 235.5–237 | 2 | N | −20.9 | −32.1 | 0.8 |
| AO.A2 | AO.A | 235.5–237 | 4 | N | −28.3 | −26.6 | 2.6 |
| AO.B2 | AO.B | 220–221.5 | 1 | N | −21.9 | −61.0 | 0.3 |
| AO.B2 | AO.B | 220–221.5 | 2 | N | −18.6 | −36.2 | 0.4 |
| AO.B2 | AO.B | 220–221.5 | 4 | N | −22.9 | −25.7 | 1.2 |
| AO.C2 | AO.C | 246–249 | 1 | N | −14.1 | −44.3 | 0.2 |
| AO.C2 | AO.C | 246–249 | 2 | N | −20.1 | −40.0 | 0.3 |
| AO.C2 | AO.C | 246–249 | 4 | N | −30.6 | −40.7 | 0.7 |

EXAMPLES AP1,AP2

Sulfonamide charge control agent having the structural formula:

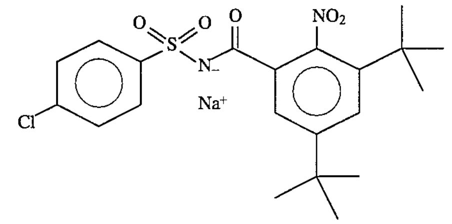

(AP)

was prepared as follows.

The sulfonamide of Examples T1–T2 (40.80 grams, 0.10 mol) was admixed with 4.2 grams (0.105 mol) of NaOH and 1 liter of water. The reaction mixture was heated to boiling, with stirring, refluxed for 20 minutes and cooled. Precipitate was collected, washed with water and dried. The solid was extracted with 400 ml of methanol and insoluble material was filtered off. The filtrate was concentrated and dried, then recrystallized from methyl ethyl ketone (filtered hot through supercel). Yield was 14.1 grams (32.8%). Melting point was 345°–347° C. Elemental analysis found C=58.44, H=5.78, N=3.37, Cl=8.52, S=6.22, Na =5.1. This compares to calculated values for $C_{21}H_{25}ClNNaO_3S$ of C=58.67, H=5.86, N=3.26, Cl=8.25, S=7.46, Na=5.35. An NMR spectrum was obtained in deuterated dimethylsulfoxide, which agreed with the structure of the expected product.

The same procedures were substantially followed in the preparation of toners and developers and in evaluating materials as described in Examples A, except that only colorless toners were produced. Results are presented in Tables 6–7.

EXAMPLES AQ1,AQ2

Sulfonamide charge control agent having the structural formula:

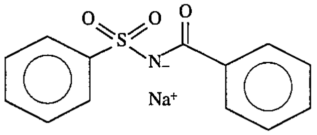

(AQ)

was prepared as follows.

A mixture of 2.61 grams (0.01 mol) of N-benzoylbenzenesulfonamide, 0.84 grams (0.01 mol) $NaHCO_3$ in about 50 ml of water, was prepared and stirred with warming. Foaming was observed. The reaction mixture was filtered and the filtrate was concentrated to dryness. Yield was 2.06 grams (79.25%). Melting point was in excess of 250° C. Elemental analysis found C=54.72, H=3.56, N=5.06, S=11.24, Na=7.9. This compares to calculated values for $C_{13}H_{10}NO_3SNa$ of C=55.12, H=3.56, N=4.94, S=11.32, Na=8.12. An NMR spectrum, in $D_2O$, was obtained which agreed with the structure of the expected product.

The same procedures were substantially followed in the preparation of toners and developers and in evaluating materials as described in Examples A, except that only colorless toners were produced. Results are presented in Tables 6–7.

EXAMPLES AR1,AR2

Sulfonamide charge control agent having the structural formula:

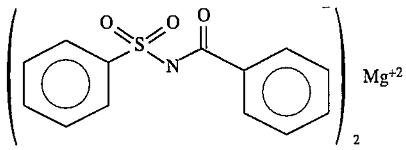

(AR)

was prepared as follows.

The sulfonamide of Examples Z1–Z2 (26.13 grams, 0.10 mol), $MgCO_3$ (4.22 grams, 0.05 mol) and 375 ml of water were placed in a flask and heated with stirring for 3 hours; at which time the reaction mixture was a clear, light yellow. The reaction mixture was cooled in an ice bath and a fluffy white precipitate formed. The solid was filtered out and the solution rotary evaporated providing a hard white solid. Yield was 20.14 grams (73.9%). Melting point was in excess of 400° C. Elemental analysis found C=57.00, H=3.77, N=5.27, S=11.09, Mg=4.1. This compares to calculated values for $(C_{13}H_{10}NO_3S)_2Mg$ of C=57.31, H=3.70, N=5.14, S=11.77, Mg=4.46.

The same procedures were substantially followed in the preparation of toners and developers and in evaluating materials as described in Examples A, except that only colorless toners were produced.

TABLE 6

Developer Using PMMA Coated Carrier

| Ex | CCA | m.p. (°C.) | Conc (pph) | P/S | Q/m (μc/g) 2 min | Q/m (μg/c) 10 min | T.O. (mg admix) |
|---|---|---|---|---|---|---|---|
| AP1 | AP | 345–347 | 1 | Y | −25.0 | −21.9 | 3.3 |
| AP1 | AP | 345–347 | 2 | Y | −24.4 | −20.0 | 1.6 |
| AP1 | AP | 345–347 | 4 | Y | −19.0 | −17.6 | 1.8 |
| AQ1 | AQ | — | 1 | Y | −14.6 | −19.3 | 8.5 |
| AQ1 | AQ | — | 2 | Y | −16.6 | −20.1 | 23.2 |
| AQ1 | AQ | — | 4 | Y | −16.7 | −15.5 | 22.4 |
| AR1 | AR | — | 1 | Y | −21.4 | −31.2 | 8.0 |
| AR1 | AR | — | 2 | Y | −23.6 | −24.5 | 11.3 |
| AR1 | AR | — | 4 | Y | −24.2 | −21.6 | 17.1 |

TABLE 7

Developer Using Modified Kynar Carrier

| Ex | CCA | m.p. (°C.) | Conc (pph) | P/S | 2 min | 10 min | T.O. (mg admix) |
|---|---|---|---|---|---|---|---|
| AP2 | AP | 345–347 | 1 | Y | −6.8 | −32.6 | 1.5 |
| AP2 | AP | 345–347 | 2 | Y | −6.7 | −32.6 | 1.2 |
| AP2 | AP | 345–347 | 4 | Y | −7.3 | −30.0 | 1.4 |
| AQ2 | AQ | — | 1 | Y | −1.9 | −27.7 | 6.2 |
| AQ2 | AQ | — | 2 | Y | −1.4 | −14.4 | 26.0 |
| AQ2 | AQ | — | 4 | Y | POS | −7.4 | — |
| AR2 | AR | — | 1 | Y | −6.3 | −45.9 | 2.0 |
| AR2 | AR | — | 2 | Y | −4.0 | −26.1 | 2.0 |
| AR2 | AR | — | 4 | Y | −6.7 | −22.7 | 5.5 |

EXAMPLES AS1,AS2

Sulfonamide charge control agent having the structural formula:

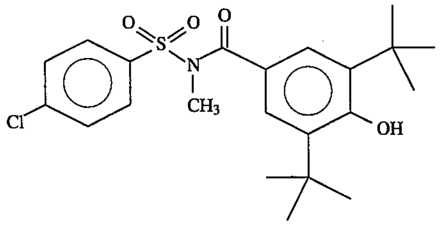

(AS)

was prepared as follows.

N-Methyl-4-chlorobenzenesulfonamide (20.57 grams, 0.10 mol) and 3,5-di-t-butyl-4-hydroxybenzoyl chloride (26.87 grams, 0.10 mol) were admixed with toluene (200 ml) in a flask and refluxed for 18.5 hours. The reaction mixture was poured into 600 ml ligroine (bp=35°–60° C.). A white solid crystallized, was collected, washed with more ligroine, dried, recrystallized from $CH_3CN$, collected and dried. Yield was 20.1 grams (45.89%). Melting point was 169°–172° C. Elemental analysis found C=60.17, H=6.19, N=3.36, Cl=8.22, S=8.24. This compares to calculated values for $C_{22}H_{28}ClNO_4S$ of C=60.33, H=6.44, N=3.20, Cl=8.09, S=7.32. An NMR spectrum, in deuterated chloroform, was obtained which agreed with the structure of the expected product.

The same procedures were substantially followed in the preparation of toners and developers and in evaluating materials as described in Examples A, except that only colorless toners were produced. Results are presented in Tables 8–9.

EXAMPLES AT1,AT2-AU1,AU2

The same procedures were substantially followed as described in Examples AS1–AS2, except that starting materials in the aroylsulfonamide preparation were different. Results are presented in Tables 8–9. Sulfonamides utilized in the examples are indicated by the designations on the following structural formulas:

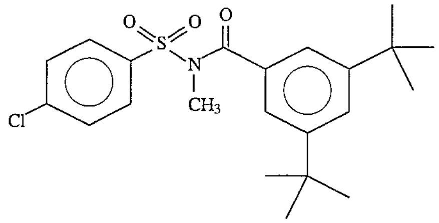
(AT)

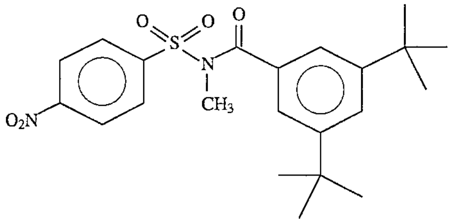
(AU)

TABLE 8

| Developer Using PMMA Coated Carrier | | | | | | | |
|---|---|---|---|---|---|---|---|
| Ex | CCA | m.p. (°C.) | Conc (pph) | P/S | 2 min | 10 min | T.O. (mg admix) |
| AS1 | AS | 169–172 | 1 | N | −16.0 | −42.8 | 1.9 |
| AS1 | AS | 169–172 | 2 | N | −16.5 | −43.6 | 2.9 |
| AS1 | AS | 169–172 | 4 | N | −16.0 | −44.5 | 4.4 |
| AT1 | AT | 152.5–155 | 1 | N | −15.8 | −48.2 | 2.5 |
| AT1 | AT | 152.5–155 | 2 | N | −13.9 | −51.3 | 3.9 |
| AT1 | AT | 152.5–155 | 4 | N | −16.0 | −49.8 | 3.6 |
| AU1 | AU | 187–188 | 1 | Y | −14.5 | −46.0 | 5.0 |
| AU1 | AU | 187–188 | 2 | Y | −15.6 | −48.3 | 6.7 |
| AU1 | AU | 187–188 | 4 | Y | −15.8 | −50.8 | 6.7 |

TABLE 9

| Developer Using Modified Kynar Carrier | | | | | | | |
|---|---|---|---|---|---|---|---|
| Ex | CCA | m.p. (°C.) | Conc (pph) | P/S | 2 min | 10 min | T.O. (mg admix) |
| AS2 | AS | 169–172 | 1 | N | −4.8 | −58.6 | 0.6 |
| AS2 | AS | 169–172 | 2 | N | −3.5 | −54.2 | 0.3 |
| AS2 | AS | 169–172 | 4 | N | −3.5 | −59.7 | 0.5 |
| AT2 | AT | 152.5–155 | 1 | N | −10.2 | −73.7 | 0.2 |
| AT2 | AT | 152.5–155 | 2 | N | −6.4 | −67.3 | 0.2 |
| AT2 | AT | 152.5–155 | 4 | N | −7.2 | −68.2 | 0.3 |

TABLE 9-continued

| Developer Using Modified Kynar Carrier | | | | | | | |
|---|---|---|---|---|---|---|---|
| Ex | CCA | m.p. (°C.) | Conc (pph) | P/S | 2 min | 10 min | T.O. (mg admix) |
| AU2 | AU | 187–188 | 1 | Y | −13.8 | −63.7 | 0 |
| AU2 | AU | 187–188 | 2 | Y | −13.4 | −64.6 | 0 |
| AU2 | AU | 187–188 | 4 | Y | −13.6 | −71.7 | 0.1 |

EXAMPLES AV1,AV2

Sulfonamide charge control agent having the structural formula:

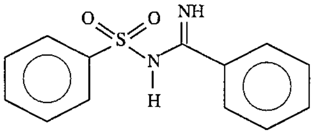
(AV)

was prepared as follows.

To a solution of N-(phenylsulfonyl)benzenecarboximidoyl chloride (8.39 grams, 0.03 mol) in dichloromethane (50 ml) was added concentrated $NH_4OH$ (50 ml). The reaction mixture was stirred for about 10 minutes while an exothermic reaction occurred. The reaction mixture was then heated on a steam bath to drive off $CH_2Cl_2$. A solid crystallized, was collected, washed with water, recrystallized from methanol and dried in a vacuum oven. Yield was 5.9 grams (75.5%). Melting point was 150°–152° C. Elemental analysis found C=60.01, H=4.63, N=10.63, S=12.10. This compares to calculated values for $C_{13}H_{12}N_2O_2S$ of C=59.98, H=4.65, N=10.76, S=12.32. An NMR spectrum was obtained in deuterated dimethylsulfoxide, which agreed with the structure of the expected product.

The same procedures were substantially followed in the preparation of toners and developers and in evaluating materials as described in Examples A, except that only colorless toners were produced. Results are presented in Tables 10–11.

EXAMPLES AX1,AX2-BA1,BA2

In AX1, AX2; AY1, AY2; and BA1, BA2; the same procedures were substantially followed as described in Examples AV1–AV2, except that starting materials in the aroylsulfonamide preparation were different. Examples AZ1,AZ2 were prepared from benzamidine.HCl and para-toluene sulfonyl chloride in accord with a general procedure described in Journal of the American Chemical Society, Vol. 64, (1942) p. 2763 and following a more specific procedure reported in Zh. Org. Khim., Vol 11, No. 1, (1975) p. 113. Results are presented in Tables 10–11.

Sulfonamides utilized in these examples are indicated by the designations on the following structural formulas:

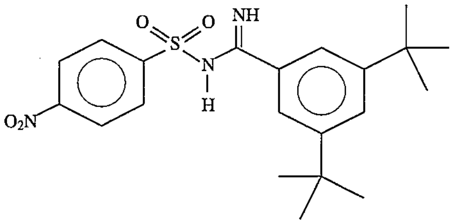
(AX)

-continued

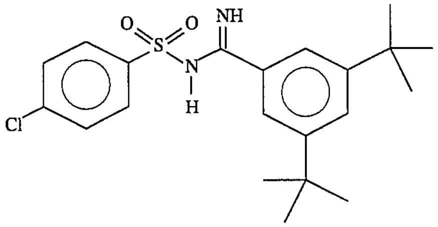

(AY)

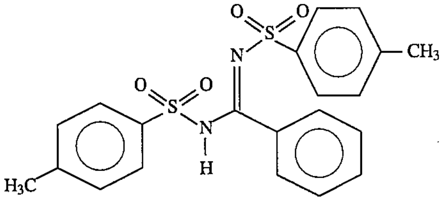

(AZ)

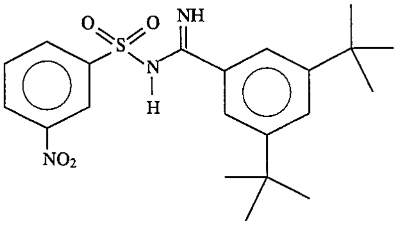

(BA)

TABLE 10

Developer Using PMMA Coated Carrier

| Ex | CCA | m.p. (°C.) | Conc (pph) | P/S | 2 min | 10 min | T.O. (mg admix) |
|---|---|---|---|---|---|---|---|
| AV1 | AV | 150–152 | 1 | N | -8.5 | -36.5 | 13.0 |
| AV1 | AV | 150–152 | 2 | N | -12.9 | -46.7 | 7.0 |
| AV1 | AV | 150–152 | 4 | N | -15.0 | -43.8 | 8.2 |
| AX1 | AX | 239–240.5 | 1 | N | -14.8 | -42.3 | 1.8 |
| AX1 | AX | 239–240.5 | 2 | N | -21.4 | -38.5 | 1.1 |
| AX1 | AX | 239–240.5 | 4 | N | -26.1 | -33.0 | 0.8 |
| AY1 | AY | 184–185 | 1 | N | -12.4 | -47.3 | 6.2 |
| AY1 | AY | 184–185 | 2 | N | -10.7 | -46.1 | 3.2 |
| AY1 | AY | 184–185 | 4 | Y | -11.2 | -46.8 | 4.3 |
| AZ1 | AZ | 156–158 | 1 | N | -14.5 | -36.3 | 4.7 |
| AZ1 | AZ | 156–158 | 2 | N | -16.0 | -32.2 | 1.4 |
| AZ1 | AZ | 156–158 | 4 | N | -16.5 | -28.8 | 2.7 |
| BA1 | BA | 159–161 | 1 | N | -13.1 | -50.9 | 5.9 |
| BA1 | BA | 159–161 | 2 | N | -13.2 | -47.5 | 4.8 |
| BA1 | BA | 159–161 | 4 | N | -14.9 | -47.9 | 3.4 |

TABLE 11

Developer Using Modified Kynar Carrier

| Ex | CCA | m.p. (°C.) | Conc (pph) | P/S | 2 min | 10 min | T.O. (mg admix) |
|---|---|---|---|---|---|---|---|
| AV2 | AV | 150–152 | 1 | N | -14.8 | -68.5 | 0.1 |
| AV2 | AV | 150–152 | 2 | N | -17.6 | -69.5 | 0.2 |
| AV2 | AV | 150–152 | 4 | N | -16.0 | -60.1 | 0.2 |
| AX2 | AX | 239–240.5 | 1 | N | -13.4 | -60.6 | 0.3 |
| AX2 | AX | 239–240.5 | 2 | N | -22.8 | -64.7 | 0.3 |
| AX2 | AX | 239–240.5 | 4 | N | -30.7 | -58.1 | 0.3 |
| AY2 | AY | 184–185 | 1 | N | -16.0 | -69.2 | 0.2 |
| AY2 | AY | 184–185 | 2 | N | -14.2 | -69.0 | 0.4 |
| AY2 | AY | 184–185 | 4 | Y | -11.6 | -74.2 | 0.4 |
| AZ2 | AZ | 156–158 | 1 | N | -13.2 | -54.2 | 0.4 |
| AZ2 | AZ | 156–158 | 2 | N | -12.0 | -53.4 | 0.3 |
| AZ2 | AZ | 156–158 | 4 | N | -11.4 | -40.2 | 0.2 |
| BA2 | BA | 159–161 | 1 | N | -10.5 | -76.8 | 0.0 |
| BA2 | BA | 159–161 | 2 | N | -8.3 | -88.5 | 0.2 |
| BA2 | BA | 159–161 | 4 | N | -10.6 | 81.3 | 0.0 |

Sulfonamide charge control agent having the structural formula:

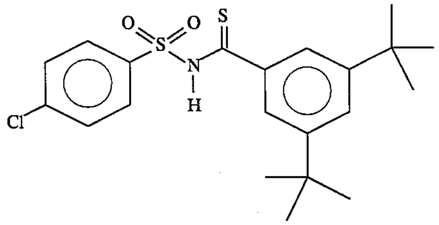

(BB)

was prepared as follows.

N-(4-Chlorobenzenesulfonyl)-3,5-di-t-butylbenzenecarboximoyl chloride was first prepared in accordance with the following procedure:

A mixture of 30.5 grams (0.075 mol) of N-(3,5-di-t-butylbenzoyl)-4-chlorobenzene-sulfonamide and 17.13 grams (0.082 mol) $PCl_5$ was heated in a 170° C. bath with stirring for 3 hours. The reaction mixture was then concentrated on a steam bath under vacuum. Heptane was added to bring the total volume of the reaction mixture to 200 ml. The reaction mixture was filtered through supercel and cooled in a dry ice/isopropanol bath. A white solid crystallized, was collected, washed with Ligroine (bp=35°–60° C.) and dried. Yield was 17.14 grams (53.6%). Melting point was 91°–92.5° C. Elemental analysis found C=58.78, H=5.81, N=3.12, Cl=16.16, S=7.77. This compares to calculated values for $C_{21}H_{25}Cl_2NO_2S$ of C=59.15, H=5.91, N=3.28, Cl=16.63, S=7.52. An NMR spectrum was obtained in deuterated chloroform, which agreed with the structure of the expected product.

To a solution of 21.62 grams (0.09 mol) of $Na_2S.9H_2O$ in 150 ml of water, was added in a stream over about 2 minutes, a solution of 31.98 grams (0.075) of N-(4-chlorobenzenesulfonyl)-3,5-di-t-butylbenzenecarboximoyl chloride in 150 ml of tetrahydrofuran. A mildly exothermic reaction occurred and the reaction mixture became green-yellow. The reaction mixture was stirred for about 2 hours then acidified with concentrated HCl (12 ml). The reaction mixture became bright orange and organic and aqueous layers separated. The organic layer was separated, washed with water and dichloromethane was added. The organic layer was separated, dried over $MgSO_4$ and concentrated as an orange-yellow solid residue. The residue was recrystallized from 240 ml of 3:1 heptane:toluene. Yellow needles were collected, washed with Ligroine (bp=35°–60° C.) and dried. Yield was 22.9 grams (72.0%). Melting point was 177°–179° C. Elemental analysis found C=59.37, H=6.24, N=3.26, Cl=8.43, S=14.98. This compares to calculated values for $C_{21}H_{26}ClNO_2S_2$ of C=59.49, H=6.18, N=3.30, Cl=8.36, S=15.12. An NMR spectrum was obtained in which agreed with the structure of the expected product.

The same procedures were substantially followed in the preparation of toners and developers and in evaluating materials as described in Examples A, except that only colorless toners were produced. Results are presented in Tables 12–13.

EXAMPLES BC1,BC2

The same procedures were substantially followed as described in Examples BB, except that starting materials in the carbonothionylsulfonamide preparation were different. Results are presented in Tables 12–13. The structural formula of the sulfonamides utilized in Examples BC is:

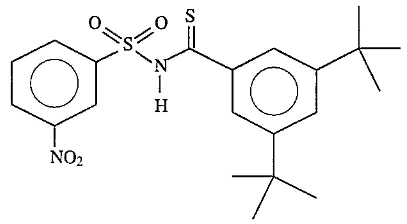
(BC)

TABLE 12

| Developer Using PMMA Coated Carrier | | | | | | | |
|---|---|---|---|---|---|---|---|
| Ex | CCA | m.p. (°C.) | Conc (pph) | P/S | 2 min | 10 min | T.O. (mg admix) |
| BB1 | BB | 177–179 | 1 | N | −16.8 | −49.8 | 1.5 |
| BB1 | BB | 177–179 | 2 | N | −20.9 | −49.2 | 2.1 |
| BB1 | BB | 177–179 | 4 | N | −23.9 | −44.3 | 3.2 |
| BC1 | BC | 140–142 | 1 | N | −22.4 | −49.1 | 1.5 |
| BC1 | BC | 140–142 | 2 | N | −19.0 | −37.9 | 1.8 |
| BC1 | BC | 140–142 | 4 | N | −29.4 | −36.6 | 6.3 |

TABLE 13

| Developer Using Modified Kynar Carrier | | | | | | | |
|---|---|---|---|---|---|---|---|
| Ex | CCA | m.p. (°C.) | Conc (pph) | P/S | 2 min | 10 min | T.O. (mg admix) |
| BB2 | BB | 177–179 | 1 | N | −13.7 | −66.8 | 0.3 |
| BB2 | BB | 177–179 | 2 | N | −17.6 | −62.4 | 0.3 |
| BB2 | BB | 177–179 | 4 | N | −27.9 | −57.8 | 0.3 |
| BC2 | BC | 140–142 | 1 | N | −25.9 | −64.4 | 0.2 |
| BC2 | BC | 140–142 | 2 | N | −23.7 | −58.5 | 0.0 |
| BC2 | BC | 140–142 | 4 | N | −41.2 | −57.6 | 0.0 |

EXAMPLES BG1,BG2

Sulfonamide charge control agent having the structural formula:

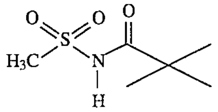
(BG)

was prepared as follows.

A mixture of 24.1 grams (0.20 mol) of pivaloyl chloride, 19.02 grams (0.20 mol) of methanesulfonamide, and 31.64 grams (0.40 mol) of pyridine was heated on a steam bath for 1.5 hours. The reaction mixture was then taken up in $CH_2Cl_2$, washed twice with dilute HCl, washed once with water, dried over $MgSO_4$, concentrated, recrystallized from toluene, collected, washed with Ligroine (bp=35°–60° C.) and dried. Yield was 17.7 grams (49.38%). Melting point=128°–129.5° C. Elemental analysis found C=40.31, H=7.20, N=7.91, S=18.20. This compares to calculated values for $C_6H_{13}NO_3S$ of C=40.21, H=7.31, N=7.81, S=17.89. An NMR spectrum was obtained in which agreed with the structure of the expected product.

The same procedures were substantially followed in the preparation of toners and developers and in evaluating materials as described in Examples A, except that only colorless toners were produced. Results are presented in Tables 16–17.

EXAMPLES BH1,BH2

The same procedures were substantially followed as described in Examples BG, except that starting materials in the aroylsulfonamide preparation were different. Results are presented in Tables 16–17. Sulfonamides utilized in the examples are indicated by the designations on the following structural formulas:

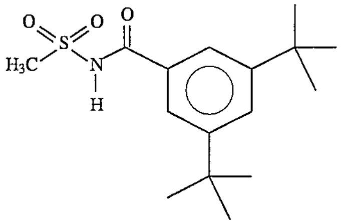
(BH)

TABLE 16

Developer Using PMMA Coated Carrier

| Ex | CCA | m.p. (°C.) | Conc (pph) | P/S | 2 min | 10 min | T.O. (mg admix) |
|---|---|---|---|---|---|---|---|
| BG1 | BG | 128–129.5 | 1 | N | −12.0 | −21.4 | 3.2 |
| BG1 | BG | 128–129.5 | 2 | N | −11.7 | −19.7 | 4.6 |
| BG1 | BG | 128–129.5 | 4 | N | −11.5 | −17.7 | 4.3 |
| BH1 | BH | 207–209 | 1 | N | −15.3 | −32.8 | 1.2 |
| BH1 | BH | 207–209 | 2 | N | −16.0 | −32.8 | 1.8 |
| BH1 | BH | 207–209 | 4 | N | −23.8 | −38.2 | 1.1 |

TABLE 17

Developer Using Modified Kynar Carrier

| Ex | CCA | m.p. (°C.) | Conc (pph) | P/S | 2 min | 10 min | T.O. (mg admix) |
|---|---|---|---|---|---|---|---|
| BG2 | BG | 128–129.5 | 1 | N | −1.5 | −46.5 | 0.6 |
| BG2 | BG | 128–129.5 | 2 | N | −1.7 | −40.0 | 0.7 |
| BG2 | BG | 128–129.5 | 4 | N | −1.6 | −29.4 | 1.0 |
| BH2 | BH | 207–209 | 1 | N | −10.2 | −49.5 | 0.3 |
| BH2 | BH | 207–209 | 2 | N | −9.5 | −45.7 | 0.3 |
| BH2 | BH | 207–209 | 4 | N | −15.1 | −37.0 | 0.5 |

Comparative Examples

COMPARATIVE EXAMPLES 1*a*,1*b*

Toners and developers were prepared and evaluated in the same manner as in Examples A1–A2, with the exception that no charge control agent was used.

COMPARATIVE EXAMPLES 2*a*,2*b*

Saccharin (ortho-benzoic sulfimide), which has the structural formula:

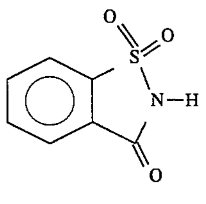

was purchased from Aldrich Chemical Company of Milwaukee, Wis. Toners and developers were prepared and evaluated in the same manner as in Examples A, with the exception that saccharin was used in place of sulfonamide charge control agent. Results are presented in Tables 18–19.

COMPARATIVE EXAMPLES 3*a*,3*b*

1-(2-Hydroxyphenyl)-3-(3,5-di-t-butylphenyl)-1,3-propanedione, which has the structural formula:

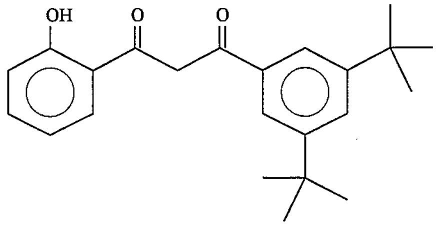

was prepared utilizing the following reaction scheme:

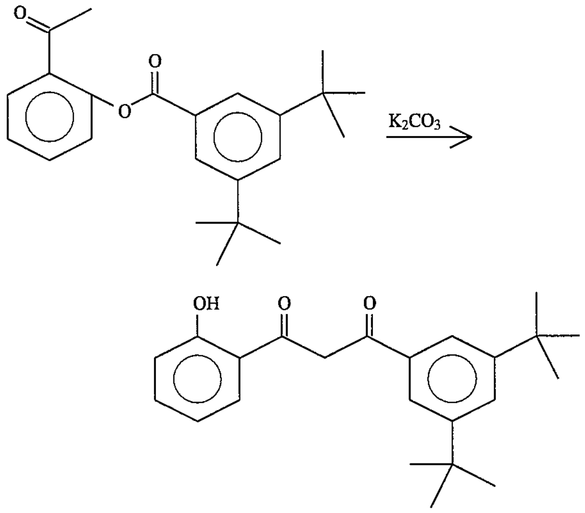

A mixture of 2'-(3,5-di-t-butylbenzoyloxy)acetophenone (55.0 g, 0.156 mol), $K_2CO_3$ (165 g), and toluene (550 ml) was prepared and heated on a steam bath with stirring. Within about two hours, a considerable amount of yellow solid had formed. The heating was continued for a total of about 21 hours. The reaction mixture was filtered hot. The solid collected was washed with ligroine (bp=35°–60° C.), dried, slurried in water, collected, and washed with a 1:1 mixture of acetic acid and water. The solid became taffy-like. The aqueous phase was decanted and the product was washed with water, and recrystallized in about 300 ml of ethanol. Solid in the form of yellow needles was collected and dried. The solid was then dissolved in dichloromethane and the solution was filtered to remove water soluble salts. The filtrate was washed with water, dried over $MgSO_4$ and concentrated. Oily residue was obtained which crystallized on cooling. This solid was recrystallized from 50 ml of ethanol. The precipitate was collected and dried. Yield was 20.3 grams (36.9%). Melting point was 92°–94° C. (Began to melt at 75° C. then solidified. Completely melted at 92°–94° C.). Elemental analysis found C=78.37, H=7.93. This compares to calculated values for $C_{22}H_{28}O_3$ of C=78.38, H=8.01. An NMR spectrum, in deuterated chloroform, was obtained which agreed with the structure of the expected product.

Toners and developers were prepared and evaluated in the same manner as in Examples A1A2, with the exception that 1-(2-hydroxyphenyl)-3-(3,5-di-t-butylphenyl)-1,3-propanedione was used in place of sulfonamide charge control agent. Results are reported in Tables 18–19.

COMPARATIVE EXAMPLES 4*a*,4*b*

Bis{1-(2-hydroxyphenyl)-3-(4-t-butylphenyl)-1,3-propanedionato}zinc, which has the structural formula:

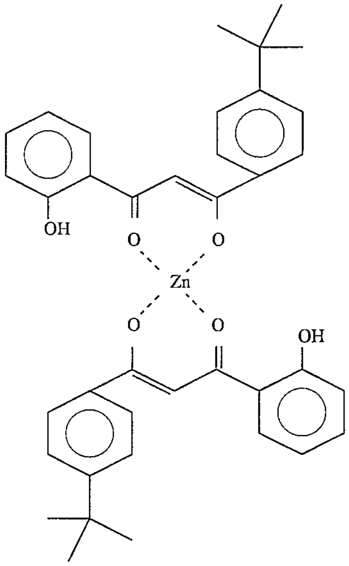

was prepared utilizing the following reaction scheme:

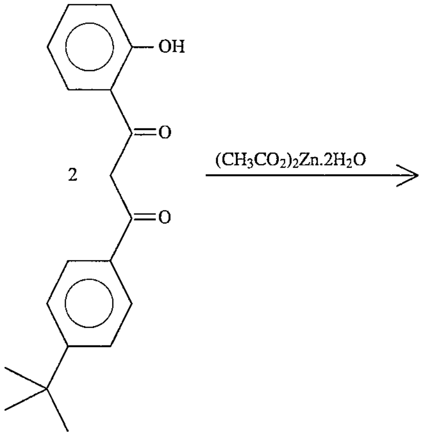

-continued

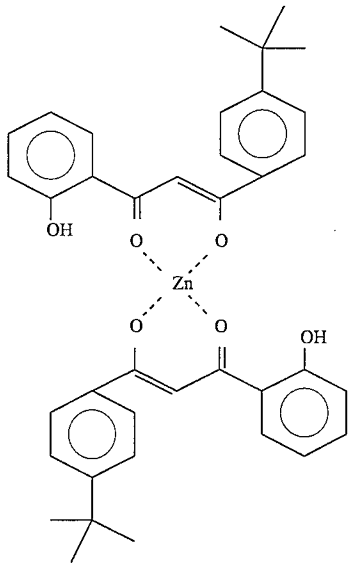

1-(2-hydroxyphenyl)-3-(4-t-butylphenyl)-1,3-propanedione was prepared by the procedure described in Comparative Examples 4, with the exception that 2'-(4-t-butylbenzoyloxy)aceptophenone was substituted for 2'-(3,5-di-t-butylbenzoyloxy)acetophenone.

A solution of 1-(2-hydroxyphenyl)-3-(4-t-butylphenyl)-1,3-propanedione (2.96 g, 0.01 mol) in methanol (50 ml) was prepared with heating. To this solution, was added a solution of zinc acetate dihydrate (1.11 g, 5 mmol) in methanol (10 ml), which had been preheated. The resulting reaction mixture was heated on a steam bath for 15 minutes. A solid crystalline precipitate that formed was filtered hot, washed with methanol and dried. Yield was 1.17 grams. Melting point was 126°–128° C. (The melt recrystallized to provide a product with a melting point in excess of 250° C.). Elemental analysis found C=69.19, H=5.68, Zn=11.6. This compares to calculated values for $C_{38}H_{38}O_6Zn$ of C=69.57, H=5.84, Zn=9.97. An NMR spectrum, in deuterated chloroform, was obtained which agreed with the structure of the expected product.

Toners and developers were prepared and evaluated in the same manner as in Examples A1, A2, with the exception that Bis{1-(2-hydroxyphenyl)-3-(4-t-butyphenyl)-1,3-propanedionato}zinc was used in place of sulfonamide charge control agent. Results are reported in Tables 18–19.

COMPARATIVE EXAMPLES 5*a*,5*b*

3,5-Di-t-butyl-4-hydroxybenzenesulfonamide has the structural formula

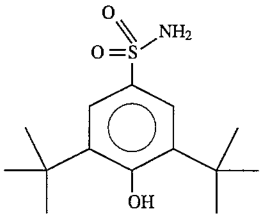

and was prepared as follows.

3,5-Di-t-butyl-4-hydroxybenzenesulfonyl chloride was prepared according to the procedure of U.S. Pat. No. 5,157,156 to Giodana et al.

A solution of 149.5 grams (0.49 mol) of 3,5-di-t-butyl-4-hydroxybenzenesulfonyl chloride in 1700 ml of methylene chloride was treated with ammonia for 35 minutes. The milky organic layer was concentrated to dryness and the solid residue was taken up in acetone, filtered and concentrated. The residue was taken up in ether, washed with water and dried over $MgSO_4$ and concentrated. The residue was recrystallized from 600 ml of isopropanol to give 99.0 grams of product (70.8% of theory). Melting point=166°–168° C. Elemental analysis found C=58.55, H=8.07, N=4.98, S=10.93. This compares to calculated values for $C_{14}H_{23}NO_3S$ of C=58.92, H=8.12, N=4.91, S =11.23. An NMR spectrum was obtained which agreed with the structure of the expected product.

Toners and developers were prepared and evaluated in the same manner as in Examples B, with the exception of the different charge control agent. Results are reported in Tables 18–19.

TABLE 18

Developer Using PMMA Coated Carrier

| Com Ex | m.p. (°C.) | Conc wgt % | P/S | 2 min | 10 min | T.O. (mg admix) |
|---|---|---|---|---|---|---|
| 1a | — | — | — | −7.8 | −49.8 | 4.7 |
| 2a | 228 | 1 | N | −16.4 | −28.1 | 24.6 |
| 2a | 228 | 2 | N | −18.8 | −30.4 | 13.5 |
| 2a | 228 | 4 | N | −28.1 | −36.6 | 5.0 |
| 3a | 92–94 | 1 | N | −10.8 | −37.3 | 1.8 |
| 3a | 92–94 | 2 | N | −11.0 | −35.4 | 2.1 |
| 3a | 92–94 | 4 | N | −11.7 | −34.1 | 2.8 |
| 4a | 126–128 | 1 | Y | −15.5 | −35.1 | 1.5 |
| 4a | 126–128 | 2 | Y | −15.2 | −34.1 | 3.9 |
| 4a | 126–128 | 4 | Y | −15.2 | −33.7 | 2.8 |
| 5a | 166–168 | 1 | N | −16.7 | −44.5 | 0.8 |
| 5a | 166–168 | 2 | N | −17.4 | −47.1 | 3.1 |
| 5a | 166–168 | 4 | N | −17.8 | −48.9 | 2.2 |

TABLE 19

Developer Using Modified Kynar Carrier

| Com Ex | m.p. (°C.) | Conc wgt % | P/S | 2 min | 10 min | T.O. (mg admix) |
|---|---|---|---|---|---|---|
| 1b | — | — | — | −7.3 | −73.2 | 0.1 |
| 2b | 228 | 1 | N | bich | −29.7 | 11.2 |
| 2b | 228 | 2 | N | bich | −4.7 | 126.3 |
| 2b | 228 | 4 | N | bich | −1.8 | 217.8 |
| 3b | 92–94 | 1 | N | −2.2 | −53.0 | 0.3 |
| 3b | 92–94 | 2 | N | −1.7 | −43.6 | 0.0 |
| 3b | 92–94 | 4 | N | −1.9 | −40.2 | 0.4 |
| 4b | 126–128 | 1 | Y | −7.3 | −46.7 | 0.3 |
| 4b | 126–128 | 2 | Y | −3.6 | −36.9 | 0.6 |
| 4b | 126–128 | 4 | Y | −4.4 | −38.7 | 0.5 |
| 5b | 166–168 | 1 | N | −13.7 | −73.2 | 0.1 |
| 5b | 166–168 | 2 | N | −12.5 | −65.3 | 0.2 |
| 5b | 166–168 | 4 | N | −10.4 | −70.6 | 0.2 |

While specific embodiments of the invention have been shown and described herein for purposes of illustration, the protection afforded by any patent which may issue upon this application is not strictly limited to a disclosed embodiment; but rather extends to all modifications and arrangements which fall fairly within the scope of the claims which are appended hereto:

What is claimed is:

1. A sulfonamide having the general structure

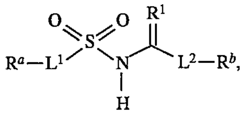

wherein $R^1$ is O or S;

$L^1$ and $L^2$ are each independently a direct link or divalent alkyl or fluoroalkyl having from 1 to 20 carbons;

$R^a$ and $R^b$ are each a ring system having as a nucleus a single six-carbon ring or from 2 to 3 fused or linked said rings, said ring system having from 6 to 34 carbons;

wherein at least one of $R^a$ and $R^b$ is phenyl having two t-alkyl substituents having from 4 to 8 carbons and a third substituent selected from the group consisting of $NO_2$, OH, $NH_2$, $N(CH_3)_2$, alkyl having from 1 to 8 carbons, and alkoxy having from 1 to 8 carbons.

2. A sulfonamide according to claim 1 wherein at least one of $R^a$ and $R^b$ is

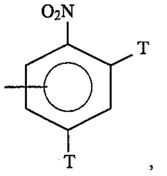

where T is tert-alkyl having from 4 to 8 carbons.

3. The sulfonamide according to claim 2 where T is a t-butyl.

4. A sulfonamide according to claim 1 wherein at least one of $R^a$ and $R^b$ includes the moiety:

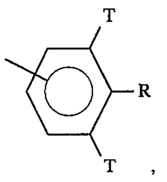

wherein

T is tertiary alkyl having from 4 to 8 carbons; and

R is selected from the group consisting of OH, $NH_2$, $N(CH_3)_2$, alkyl having from 1 to 8 carbons, and alkoxy having from 1 to 8 carbons.

5. The sulfonamide according to claim 4 where T is a t-butyl.

6. A sulfonamide according to claim 1 wherein at least one of $R^a$ and $R^b$ includes the moiety:

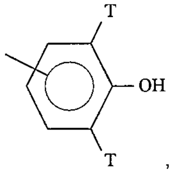

wherein T is tertiary alkyl having from 4 to 8 carbons.

7. The sulfonamide according to claim 6 where T is a t-butyl.

8. The sulfonamide according to claim 1 having the following structure:

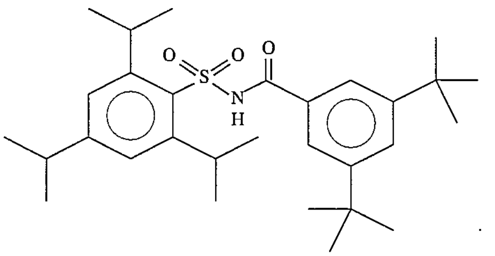

9. The sulfonamide according to claim 1 having the following structure:

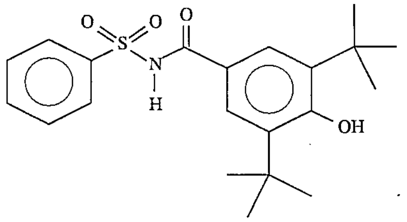

10. The sulfonamide according to claim 1 having the following structure:

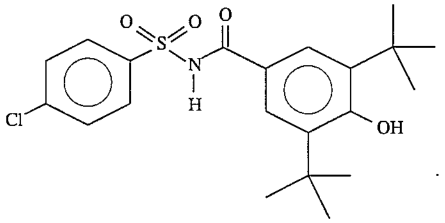

11. The sulfonamide according to claim 1 having the following structure:

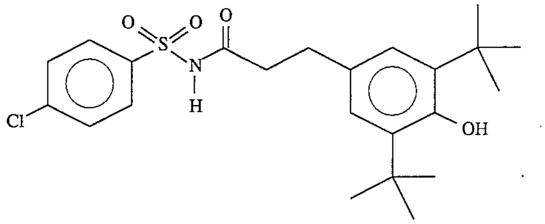

12. The sulfonamide according to claim 1 having the following structure:

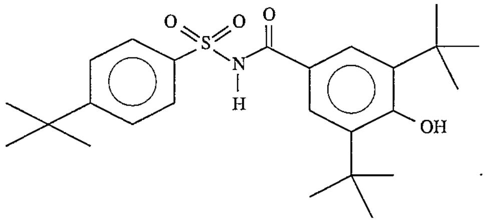

13. The sulfonamide according to claim 1 having the following structure:

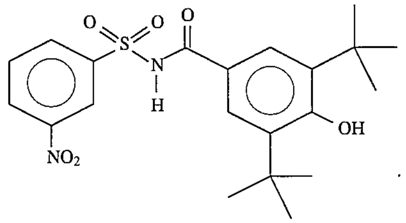

14. The sulfonamide according to claim 1 having the following structure:

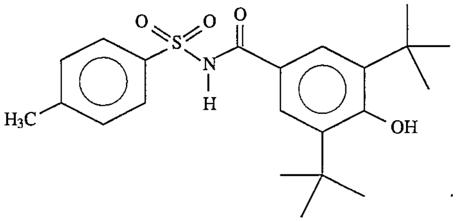

15. The sulfonamide according to claim 1 having the following structure:

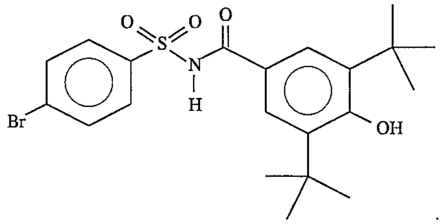

16. The sulfonamide according to claim 1 having the following structure:

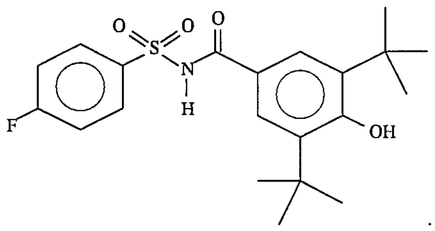

17. The sulfonamide according to claim 1 having the following structure:

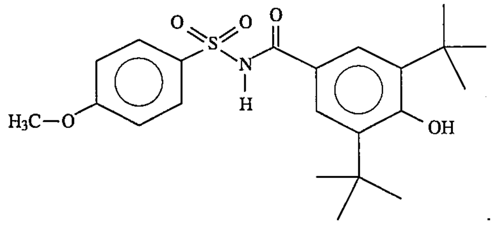

18. The sulfonamide according to claim 1 having the following structure:

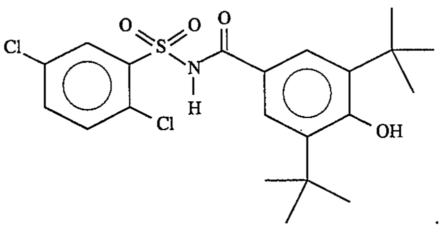

19. The sulfonamide according to claim 1 having the following structure:

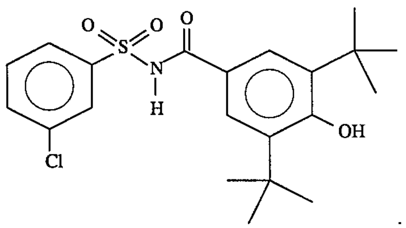

20. The sulfonamide according to claim 1 having the following structure:

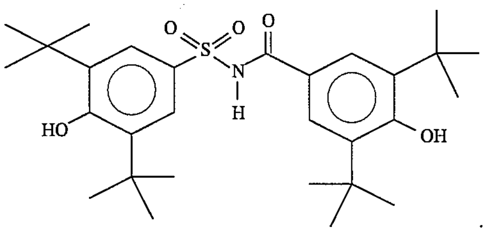

21. The sulfonamide according to claim 1 having the following structure:

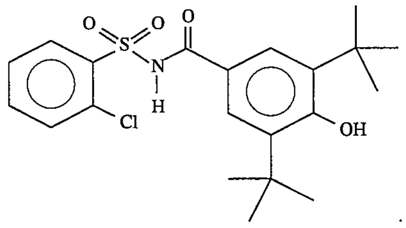

22. The sulfonamide according to claim 1 having the following structure:

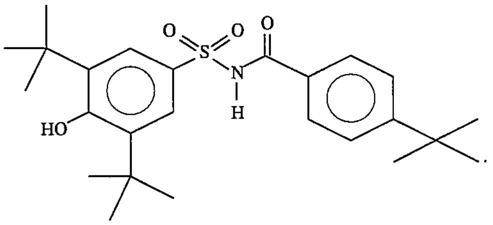

23. The sulfonamide according to claim 1 having the following structure:

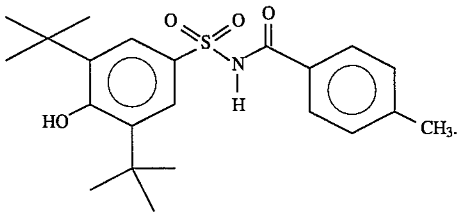

24. The sulfonamide according to claim 1 having the following structure:

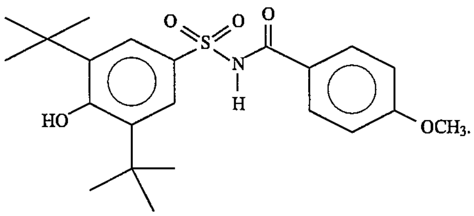

* * * * *

UNITED STATES PATENT AND TRADEMARK OFFICE
CERTIFICATE OF CORRECTION

PATENT NO. : 5,616,797
DATED : April 1, 1997
INVENTOR(S) : John C. Wilson, Peter S. Alexandrovich and Steven M. Bonser It is certified that error appears in the above-indentified patent and that said Letters Patent is hereby corrected as shown below:

Column 9, line 35

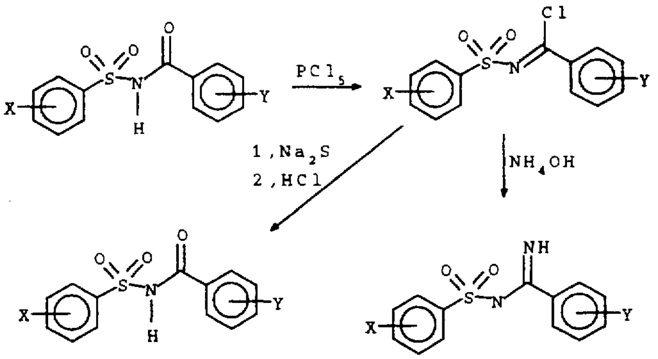

-- should read:

UNITED STATES PATENT AND TRADEMARK OFFICE

CERTIFICATE OF CORRECTION

PATENT NO. : 5,616,797

DATED : April 1, 1997

INVENTOR(S) : John C. Wilson, Peter S. Alexandrovich and Steven M. Bonser

It is certified that error appears in the above-indentified patent and that said Letters Patent is hereby corrected as shown below:

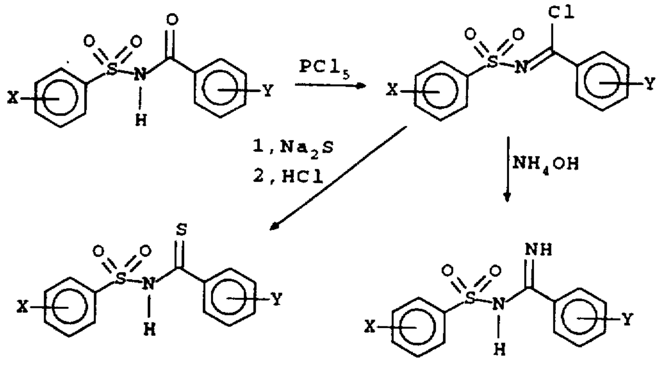

-- --

Signed and Sealed this

Ninth Day of September, 1997

Attest:

BRUCE LEHMAN

*Attesting Officer* *Commissioner of Patents and Trademarks*